United States Patent [19]
Valera et al.

[11] Patent Number: 5,985,603
[45] Date of Patent: Nov. 16, 1999

[54] $P_{2X}$ RECEPTOR DNA AND PROTEIN SEQUENCE

[75] Inventors: Soledad Valera; Gary N Buell, both of Geneva, Switzerland

[73] Assignee: Glaxo Group Limited, Greenford, United Kingdom

[21] Appl. No.: 08/750,134

[22] PCT Filed: May 24, 1995

[86] PCT No.: PCT/EP95/01968

§ 371 Date: Jan. 22, 1997

§ 102(e) Date: Jan. 22, 1997

[87] PCT Pub. No.: WO95/33048

PCT Pub. Date: Dec. 7, 1995

[30] Foreign Application Priority Data

May 27, 1994 [GB] United Kingdom .................... 9410664
Feb. 9, 1995 [GB] United Kingdom .................... 9502480

[51] Int. Cl.⁶ ........................ C12N 15/12; C07K 14/705; C07H 21/04
[52] U.S. Cl. ........................ 435/69.1; 536/23.5; 435/325; 435/252.3; 435/254.11; 435/320.1; 530/350
[58] Field of Search ..................... 530/350; 536/23.5, 536/24.31; 435/69.1, 325, 252.3, 254.11, 320.1

[56] References Cited

PUBLICATIONS

Bo et al., J. Biol. Chem., 267, 17581–17587, Sep. 5, 1992.

Saxe et al., Genes & Development, 5, 1–8, 1991.

Lewin, Science, 237, 1570, 1987.

Reeck et al., Cell, 50, 667, 1987.

Harden et al, Annu. Rev. Pharmacol. Toxicol. (1995) 35, 541–79 $P_2$–Purinergic Receptors: Subtype–Associated Signaling Responses and Structure.

*Primary Examiner*—Lorraine Spector
*Attorney, Agent, or Firm*—Nixon & Vanderhye P.C.

[57] ABSTRACT

The $P_{2X}$ receptor of ATP has been cloned and expressed by recombinant DNA technology, so the receptor can be prepared free from other ATP receptors. The $P_{2X}$ receptor enables antibodies to be prepared and is useful in screening compounds for use in a variety of diseases and conditions, including epilepsy, cognition, emesis, pain (especially migraine), asthma, peripheral vascular disease, hypertension, diseases of the immune system, irritable bowel syndrome and premature ejaculation.

12 Claims, 19 Drawing Sheets

Fig. 1A

P2xα 1 cDNA from rat vas deferens

```
  1 gccaaagctgtctgatcaccaccagggtttcctcccaaccagaccccaccatcgaacctccaactctgtcccacct      80

81 agcctgctctgtcccttaagggccgggaagcccccagtcactccactgctattgtagatgcagatgttggcctgccctga  160

161 ccatagaggccgtgggtgtcatctctgagcccctctggccacc ATG GCT CGG CGG CTG CAA GAT          230
                                                M   A   R   R   L   Q   D            7

231 GAG CTG TCA GCC TTC TTC TTT GAA TAT GAC ACT CCC CGG ATG GTG CTG GTA CGA AAC AAG   290
  8  E   L   S   A   F   F   F   E   Y   D   T   P   R   M   V   L   V   R   N   K    27

291 AAG GTG GGA GTC ATT TTC CGT CTG ATC CAG TTG GTG GTT CTG GTC TAC GTC ATT GGG TGG   350
 28  K   V   G   V   I   F   R   L   I   Q   L   V   V   L   V   Y   V   I   G   W    47

351 GTG TTT GTC TAT GAA AAA GGA TAC CAG ACC TCA AGT GAC CTC ATC AGC AGT GTG TCC GTG   410
 48  V   F   V   Y   E   K   G   Y   Q   T   S   S   D   L   I   S   S   V   S   V    67

411 AAG CTC AAG GGC TTG GCT GTG ACC CAG CTC CAG GGC CTG GGA CCC CAG GTC TGG GAC GTG   470
 68  K   L   K   G   L   A   V   T   Q   L   Q   G   L   G   P   Q   V   W   D   V    87

471 GCT GAC TAT GTC TTC CCA GCA CAC GGG GAC AGC TCC TTT GTA GTT ATG ACC AAC TTC ATC   530
 88  A   D   Y   V   F   P   A   H   G   D   S   S   F   V   V   M   T   N   F   I    107

531 GTG ACC CCT CAG CAG ACT CAA GGC CAT TGT GCA GAG AAC CCA GAA GGT GGC ATA TGC CAG   590
108  V   T   P   Q   Q   T   Q   G   H   C   A   E   N   P   E   G   G   I   C   Q    127
```

Fig. 1B

```
591  GAT GAC AGT GGC TGC ACT CCA GGA AAA GCA GAA AGG AAA GCC CAA GGT ATT CGC ACA GGC   650
128   D   D   S   G   C   T   P   G   K   A   E   R   K   A   Q   G   I   R   T   G   147

651  AAC TGT GTG CCC TTC AAT GGC ACT GTG AAG ACA TGT GAG ATC TTT GGT TGG TGT CCT GTA   710
148   N   C   V   P   F   N   G   T   V   K   T   C   E   I   F   G   W   C   P   V   167

711  GAG GTG GAT GAC AAG ATC CCA AGC CCT GCT CTT CTT CGT GAG GCT GAG AAC TTC ACC CTC   770
168   E   V   D   D   K   I   P   S   P   A   L   L   R   E   A   E   N   F   T   L   187

CCC CAG CTG GCA CAT GGC TGC TAC CCA TGC CCT CCA CAC AG     sequence of RP-2
           P   Q   L   A   H   G   C   Y   P   C   P   P   H   R 771  TTC ATC AAA AAC AGC ATC AGC TTT CCA CGC TTC AAG GTC AAC AGG CGC AAC CTG GTA GAG   830
188   F   I   K   N   S   I   S   F   P   R   F   K   V   N   R   R   N   L   V   E   207

831  GAG GTG AAC GGC ACC TAC ATG AAG AAG TGC CTC TAT CAC CCC CAG ATT CAA CAC CCC TGC   890
208   E   V   N   G   T   Y   M   K   K   C   L   Y   H   P   Q   I   Q   H   P   C   227

891  CCA GTC TTC AAC CTT GGC TAT GTG GTG CGA GAG TCA GGC CAG GAC TTC CGC AGC CTT GCT   950
228   P   V   F   N   L   G   Y   V   V   R   E   S   G   Q   D   F   R   S   L   A   247

951  GAG AAG GGT GGG GTG GTT GGT ATC ACC ATT GAC TGG AAG TGT GAT CTG GAC TGG CAC GTT   1010
248   E   K   G   G   V   V   G   I   T   I   D   W   K   C   D   L   D   W   H   V   267

1011 CGG CAC TGC AAA CCC ATC TAC CAG TTC CAC GGA CTG TAT GGG GAG AAG AAC CTG TCT CCA   1070
268   R   H   C   K   P   I   Y   Q   F   H   G   L   Y   G   E   K   N   L   S   P   287
```

Fig. 1C

```
1071 GGC TTC AAC TTC AGA TTT GCC AGG CAT TTC GTG CAG AAT GGG ACA AAC CGT CGT CAC CTC 1130
 288   G   F   N   F   R   F   A   R   H   F   V   Q   N   G   T   N   R   R   H   L  307

1131 TTC AAG GTG TTT GGG ATT CAC TTT GAT ATC CTT GTG GAT GGC AAG GCT GGG AAG TTT GAC 1190
 308   F   K   V   F   G   I   H   F   D   I   L   V   D   G   K   A   G   K   F   D  327

1191 ATC ATC CCT ACT ATG ACT ATC GGT TCT GGG ATT GGC ATC TTT GGA GTG GCC ACA GTG 1250
 328   I   I   P   T   M   T   I   G   S   G   I   G   L   P   G   V   A   T   V  347

1251 CTT TGT GAT CTC TTA TTG CTC CAC ATC CTG CCT AAG AGG CAC TAC TAC AAG CAG AAG AAG 1310
 348   L   C   D   L   L   L   L   H   I   L   P   K   R   H   Y   Y   K   Q   K   K  367

1311 TTT AAA TAT GCC GAG GAC ATG GGG CCG GGA GAG GGT GAA CAT GAC CCC GTG GCC ACC AGC 1370
 368   F   K   Y   A   E   D   M   G   P   G   E   G   E   H   D   P   V   A   T   S  387

1371 TCC ACT CTG GGC CTG CAG GAG AAC ATG AGG ACC TCC TGA ccttagtcttgagatccggacttgacgc 1437
 388   S   T   L   G   L   Q   E   N   M   R   T   S   *                              400

1438 agtgtgtggcttccggcaagggctgatgcttgagccaggcagagggcattcccagaggcttcctgcaaggcagaca 1517

1518 ccagtgccctctgttcagctcgttgattcagagctcgttcagttccacatgtccctc 1597
                                              end of rp-2 sequence -/

1598 ctgagggatgcctcctccagtttcaccaatttgggttcatatggctggccccacacatctatactctagcttgtg 1677

1678 cttaaggctcaggctgtcattgtctttcccacagcctaccctgcctagattcggcttcttccacatgtagccactagcc 1757

1758 agatgtgtcagtttgaactttaattaaatataataaaaaaaaaaaaaaaaaaaaaaaa 1837
```

Fig. 2A rat P2X clone 3

```
  1 cgcagcgagcctgccggagctgtgggtgctggagtgagctacgaccggagccgacgtggcgagggaccacagtgtccaaggc      80
 81 gcggagcggtcggcggagcc ATG GCG CAG CTG GGC TGC TCC GTG CTC ATG AAC CGC ATG GTG ACG TAC    145
                        M   A   Q   L   G   C   S   V   L   M   N   R   M   V   T   Y     15
146 GAC ACG CCG CGC ATC GTG GTC ATC CGC AGC CGT AAA GTG GGG CTC ATG AAC CGC GCG GTG GAG TAC  205
 16  D   T   P   R   I   V   V   I   R   S   R   K   V   G   L   M   N   R   A   V   E   Y   35
206 CAG CTG CTC ATC CTG GCT TAC GTC ATC GGG TGG GTG TTC GTG TGG GAA AAG GGC TAC CAG TTC     265
 36  Q   L   L   I   L   A   Y   V   I   G   W   V   F   V   W   E   K   G   Y   Q   F      55
266 GAA ACG GAC GAC TCC GTG GTC AGC GTC ACA ACC AAA GCC AAA GGT GTG GCT GTG ACC AAC AAC     325
 56  E   T   D   D   S   V   V   S   V   T   T   K   A   K   G   V   A   V   T   N   N      75
326 ACC TCT CAG CTT GGA TTC CGG ATC TGG GAC GTG GCG GAC TAT GTG ATT CCA GCT CAG GAG GAG     385
 76  T   S   Q   L   G   F   R   I   W   D   V   A   D   Y   V   I   P   A   Q   E   E      95
386 GAA AAC TCC CTC TTC ATT ATG ACC AAC ATG ATT GTC ACC GTG AAC CAG ACA CAG AGC ACC ACC     445
 96  E   N   S   L   F   I   M   T   N   M   I   V   T   V   N   Q   T   Q   S   T   T     115
446 TGT CCA GAG ATT CCT GAT AAG ACC AGC ATT TGT AAT TCA GAC GCC GAC TGC GTT CCT GGC GGC     505
116  C   P   E   I   P   D   K   T   S   I   C   N   S   D   A   D   C   V   P   G   G     135
506 TCC GTG GAC ACC CAC AGC AGT GGA GTT GCG ACT GGA AGA TGT GTT CCT TTC AAT GAG TCT         565
136  S   V   D   T   H   S   S   G   V   A   T   G   R   C   V   P   F   N   E   S         155
566 GTG AAG ACC TGT GAG GTG GCT GCT TGG TGC CCG GTG GAG AAC GAC GTT GGC GTG CCA ACG         625
156  V   K   T   C   E   V   A   A   W   C   P   V   E   N   D   V   G   V   P   T         175
626 CCG GCT TTC TTA AAG GCT GCA GAA AAC TTC ACC CTC TTG GTA AAG AAC AAC ATC TGG TAC         685
176  P   A   F   L   K   A   A   E   N   F   T   L   L   V   K   N   N   I   W   Y         195
```

Fig. 2B

```
 686 CCC AAG TTT AAC TTC AGC AAG AGG AAC ATC CTC CCC AAC ATC ACC ACG TCC TAC CTC AAA  745
 196  P   K   F   N   F   S   K   R   N   I   L   P   N   I   T   T   S   Y   L   K   215

746 TCG TGC ATT TAC AAT GCT CAA ACG GAT CCC TTC TGC CCC ATA TTC CGT CTT GGC ACA ATC  805
 216  S   C   I   Y   N   A   Q   T   D   P   F   C   P   I   F   R   L   G   T   I   235

806 GTG GGG GAC GCG GGA CAT AGC TTC CAG GAG ATG GCA GTT GAG GGA GGC ATC ATG GGT ATC  865
 236  V   G   D   A   G   H   S   F   Q   E   M   A   V   E   G   G   I   M   G   I   255

866 CAG ATC AAG TGG GAC TGC AAC CTG GAT AGA GCC TCC CTT TGC CTG CCC AGA TAT TCC      925
 256  Q   I   K   W   D   C   N   L   D   R   A   S   L   C   L   P   R   Y   S       275

926 TTC CGG CGC CTG GAC ACC CGG GAC CTG GAA CAC AAT GTG TCT CCT GGC TAC AAT TTC AGG  985
 276  F   R   R   L   D   T   R   D   L   E   H   N   V   S   P   G   Y   N   F   R   295

986 TTT GCC AAG TAC TAC AGG GAC CTG GCC GGC AAA GAG CGC ACA CTC ACC AAG GCG TAC     1045
 296  F   A   K   Y   Y   R   D   L   A   G   K   E   R   T   L   T   K   A   Y       315

1046 GGC ATC CGC TTT GAC ATC ATC GTG TTT GGA AAG GCT GGG AAG TTT GAC ATC ATC CCT ACC 1105
 316  G   I   R   F   D   I   I   V   F   G   K   A   G   K   F   D   I   I   P   T   335

1106 ATG ATC AAC GTT GGC TCT ATG TTG GCG CTC CTC TAC TAC CGG GTG GCG ACG GTC TGT GAC GTC 1165
 336  M   I   N   V   G   S   M   L   A   L   L   Y   Y   R   V   A   T   V   C   D   V  355

1166 ATA GTC CTC TAC TGC GAG CAG AAG AAA TAC AAG AAA TAT GTG                          1225
 356  I   V   L   Y   C   E   Q   K   K   Y   K   K   Y   V                           375

1226 GAA GAC TAC GAG CAG CAG GGT CTT TCG GGG GAG ATG AAC CAG TGA cgcctaaagttacattccacccc 1291
 376  E   D   Y   E   Q   Q   G   L   S   G   E   M   N   Q   *                       389
```

Fig. 2C

```
1292 gctcagcccgcgaagcagaagatggggagagatggctactgcgtctgtcactctagagaagctccagagtttcagctc 1371
1372 agttctccactccacaaatactccagggttgccaagcacatcttgttggagcccggctcttgctctgtcagatgggc 1451
1452 tccagatacaagaatcctcctgcttctgcctctaggaatgctggatcaaacatgtcactgcaatgcccattcccat 1531
1532 ggggagtttggcattttttacatttctacccttcccttttgtatacatctaaggctgcccctcagacgcaagacgttcttcc 1611
1612 acctatacaccctttaatctcactgtgtgtgggagggggtcgtttgcacacgacgcacgtggatgtctggtgtgct 1691
1692 gttggctgggccactgtggcttatacagtgtgagcgtgagcagaagggtctgagagcagagacactgctgtggc 1771
1772 ttacggacaggcccaggcctctgtccacgcacttattctctaaggaaggaggctcctcaggtgctgtcagcaggcctggg 1851
1852 acaccattcctcctcccctataatcagagaagtgtccttgtagcaaaggcaggttagctttccttttataaggctgt 1931
1932 gttgaaatgacctaggaccaaacattaaaagaaataattttttaaaaaaaaaaaaaaaaaa 1997
```

Fig. 3A rat P2X clone 6

```
1   cactgggctacagttgcctggcttacaggaactggtcctcttttcctcaagcctcattaagcagccccactccagttcttgat    80

81  ctttgtcctccagtcctgaagtcctctctcctaggctgcatccacagcccttctaagtggctgtgagcagttcctca          160

161 gt ATG AAC TGT ATA TCA GAC TTC TTC ACC TAC GAG ACT ACC AAG TCG GTG GTT GTG AAG           219
    1  M   N   C   I   S   D   F   F   T   Y   E   T   T   K   S   V   V   V   K             19

220 AGC TGG ACC ATT GGG ATC ATC AAC CGA GCC GTC CAG CTG CTG ATT ATC TCC TAC TTT GTG          279
20  S   W   T   I   G   I   I   N   R   A   V   Q   L   L   I   I   S   Y   F   V            39

280 GGG TGG GTT TTC TTG CAT GAG AAG GCC TAC CAA GTG AGG GAC ACC GCC ATT GAG TCC TCA          339
40  G   W   V   F   L   H   E   K   A   Y   Q   V   R   D   T   A   I   E   S   S            59

340 GTA GTT ACA AAG GTG AAA GGG CGC TAT GCC AAC AGA GTC ATG GAC GTG TCG GAT                  399
60  V   V   T   K   V   K   G   R   Y   A   N   R   V   M   D   V   S   D                    79

400 TAT GTG ACC CCA CCC CAG GGC ACC TCT GTC TTT GTC ATC ATC ACC AAA ATG ATC GTT ACT          459
80  Y   V   T   P   P   Q   G   T   S   V   F   V   I   I   T   K   M   I   V   T            99

460 GAA AAT CAA ATG CAA GGA TTC TGT CCA GAG AAT GAA GAG AAG TAC CGC TGT GTG TCT GAC          519
100 E   N   Q   M   Q   G   F   C   P   E   N   E   E   K   Y   R   C   V   S   D           119

520 AGC CAG TGT GGG CCT GAA CGC TTC CCA GGT GGG GGG ATC CTC ACC GGC CGC TGC GTG AAC          579
120 S   Q   C   G   P   E   R   F   P   G   G   G   I   L   T   G   R   C   V   N           139
```

Fig. 3B

```
580  TAC AGC TCT GTT CTC CGG ACC TGT GAG ATC CAG GGC TGG TGC CCC ACT GAG GTG GAC ACC  639
140   Y   S   S   V   L   R   T   C   E   I   Q   G   W   C   P   T   E   V   D   T   159

640  GTG GAG ATG CCT ATC ATG ATG GAG GCT GAG AAC TTC ACC ATT TTC ATC AAG AAC AGC ATC  699
160   V   E   M   P   I   M   M   E   A   E   N   F   T   I   F   I   K   N   S   I   179

700  CGT TTC CCT CTC TTC AAC TTT GAG AAG GGA AAC CTC CTG CCT AAC CTC ACC GAC AAG GAC  759
180   R   F   P   L   F   N   F   E   K   G   N   L   L   P   N   L   T   D   K   D   199

760  ATA AAG AGG TGC CGC TTC CAC CCT GAA AAG GCC CCA TTT TGC CCC ATC TTG AGG GTA GGG  819
200   I   K   R   C   R   F   H   P   E   K   A   P   F   C   P   I   L   R   V   G   219

820  GAT GTG GTT AAG TTT GCT GGA CAG GAT TTT GCC AAG CTG GCC CGG ACG GGT GGC GTT CTG  879
220   D   V   V   K   F   A   G   Q   D   F   A   K   L   A   R   T   G   G   V   L   239

880  GGT ATT AAG ATC GGC TGG GTG TGC GAT CTA GAC AAG GCC TGG GAC CAG TGC ATC CCT AAA  939
240   G   I   K   I   G   W   V   C   D   L   D   K   A   W   D   Q   C   I   P   K   259

940  TAT TCC TTC ACT CGG CTG GAT GGA GTT TCT GAG AAA AGC AGT GTT TCC CCT GGC TAC AAC  999
260   Y   S   F   T   R   L   D   G   V   S   E   K   S   S   V   S   P   G   Y   N   279

1000 TTC AGG TTT GCC AAA TAC TAT AAG ATG GAG AAC GGC AGC GAG TAC CGC ACA CTC CTG AAG  1059
280   F   R   F   A   K   Y   Y   K   M   E   N   G   S   E   Y   R   T   L   L   K   299

1060 GCT TTT GGC ATC CGC TTT GAT GTG CTG GTA TAT GGG AAC GCT GGC AAG TTC AAC ATC ATC  1119
300   A   F   G   I   R   F   D   V   L   V   Y   G   N   A   G   K   F   N   I   I   319
```

Fig. 3C

```
1120 CCC ACC ATT ATC AGC TCG GTG GCG GCC TTC ACT TCT GTG GGA GTG GGC ACT GTT CTC TGT 1179
 320  P   T   I   I   S   S   V   A   A   F   T   S   V   G   V   G   T   V   L   C  339

1180 GAC ATC ATC CTG CTC AAT TTC CTC AAA GGG GCT GAT CAC TAC AAA GCC AGG AAG TTT GAG 1239
 340  D   I   I   L   L   N   F   L   K   G   A   D   H   Y   K   A   R   K   F   E  359

1240 GAG GTG ACT GAG ACA ACA CTG AAG GGT ACT GCG TCA ACC AAC CCA GTG TTC GCC AGT GAC 1299
 360  E   V   T   E   T   T   L   K   G   T   A   S   T   N   P   V   F   A   S   D  379

1300 CAG GCC ACT GTG GAG AAG CAG TCT ACA GAC TCA GGG GCC TAT TCT ATT GGT CAC tagggcct 1361
 380  Q   A   T   V   E   K   Q   S   T   D   S   G   A   Y   S   I   G   H           397

1362 cttcccaggttccatgctccaccctcaggctgcagaacctgcaaacaggccactcctatctaagcagtcaggggtgggagg 1441
1442 gggagaagagggctgtattctgctgttcacccccaaagactagatccagatatctaggccctcactgttcaacagata 1521
1522 ggcaatgcttcccactaagacttgaatcttgcctcccacctgcctcccctgcttccctggatcccaggacag 1601
1602 cagcatccaccccttccaaaggattgagaaatggtagctaaggttacacccatagaaatggtagaaaaaaaaaaaaaaaaa 1681
1682 ccacacatattatcccttcccacccttaaaatcccctataagtagaaaaaaaaaaaaaaaaaaaa 1753
```

Fig. 4A

```
  1  gcctccagctgacctctggctcctctgctcctcactgcacgccctgctcctcctaaggggccaggaagcccca      80

81  gaagtctctaccatcgacgtgggtggtgtggcaccctgagagcagagggcgtgcaggggctcagttcctgagcc     160

161  cagccggccacc ATG GCA CGG CGG TTC CAG GAG GAG CTG GCC TTC CTC TTC GAG TAT         221
                  M   A   R   R   F   Q   E   E   L   A   F   L   F   E   Y           16

222  GAC ACC CCC CGC ATG GTG CTG GTG CGT AAT AAG AAG GTG GGC GTT ATC TTC CGA CTG ATC  281
      D   T   P   R   M   V   L   V   R   N   K   K   V   G   V   I   F   R   L   I    36

282  CAG CTG GTG GTC CTG GTC TAC GTC ATC GGG TGG GTG TTT CTC TAT GAG AAG GGC TAC CAG  341
      Q   L   V   V   L   V   Y   V   I   G   W   V   F   L   Y   E   K   G   Y   Q    56

342  ACC TCG AGC GGC CTC ATC AGT GTC TCT GTG AAA CTC AAG GGC CTG GCC GTG ACC CAG      401
      T   S   S   G   L   I   S   V   S   V   K   L   K   G   L   A   V   T   Q        76

402  CTC CCT GGC CTC GGC CCC CAG GTC TGG GAT GTG GCT GAC TAC GTC TTC CCA GCC CAG GGG  461
      L   P   G   L   G   P   Q   V   W   D   V   A   D   Y   V   F   P   A   Q   G    96

462  GAC AAC TCC TTC GTG GTC ATG ACC AAT TTC ATC GTG ACC CCG AAG CAG ACT CAA GGC TAC  521
      D   N   S   F   V   V   M   T   N   F   I   V   T   P   K   Q   T   Q   G   Y   116

522  TGC GCA GAG CAC CCA GAA GGG GGC ATA TGC AAG GAA GAC AGT GGC TGT ACC CCT GGG AAG  581
      C   A   E   H   P   E   G   G   I   C   K   E   D   S   G   C   T   P   G   K   136
```

Fig. 4B

```
 582 GCC AAG AGG AAG GCC CAA GGC ATC CGC ACG GGC AAG TGT GTG GCC TTC AAC GAC ACT GTG   641
 137  A   K   R   K   A   Q   G   I   R   T   G   K   C   V   A   F   N   D   T   V   156

642 AAG ACG TGT GAG ATC TTT GGC TGC CCC GTG GAG GTG GAT GAC GAC ATC CCG CGC CCT        701
 157  K   T   C   E   I   F   G   C   P   V   E   V   D   D   D   I   P   R   P        176

702 GCC CTT CTC CGA GAG GCC GAG AAC TTC ACT CTT TTC ATC AAG AAC AGC ATC AGC TTT CCA   761
 177  A   L   L   R   E   A   E   N   F   T   L   F   I   K   N   S   I   S   F   P   196

762 CGC TTC AAG GTC AAC AGG CGC AAC CTG GTG GAG GAG GTG AAT GCT GCC CAC ATG AAG ACC   821
 197  R   F   K   V   N   R   R   N   L   V   E   E   V   N   A   A   H   M   K   T   216

822 TGC CTC TTT CAC AAG ACC CTG CAC CCC CTG TGC CCA GTC TTC CAG CTT GGC TAC GTG GTG   881
 217  C   L   F   H   K   T   L   H   P   L   C   P   V   F   Q   L   G   Y   V   V   236

882 CAA GAG TCA GGC CAG AAC TTC AGC ACC CTG GCT GAG AAG GGT GGA GTT GGC ATC ACC       941
 237  Q   E   S   G   Q   N   F   S   T   L   A   E   K   G   G   V   G   I   T        256

942 ATC GAC TGG CAC TGT GAC CTG GAC TGG CAC GTA CGG CAC TGC AGA CCC ATC TAT GAG TTC  1001
 257  I   D   W   H   C   D   L   D   W   H   V   R   H   C   R   P   I   Y   E   F   276

1002 CAT GGG CTG TAC GAA GAG AAA AAT CTC TCC CCA GGC TTC AAC TTC AGG TTT GCC AGG CAC  1061
 277  H   G   L   Y   E   E   K   N   L   S   P   G   F   N   F   R   F   A   R   H   296

1062 TTT GTG GAG AAC GGG ACC AAC TAC CGT CAC CTC TTC AAG GTG TTT GGG ATT CGC TTT GAC  1121
 297  F   V   E   N   G   T   N   Y   R   H   L   F   K   V   F   G   I   R   F   D   316
```

Fig. 4C

```
1122 ATC CTG GTG GAC GGC AAG GCC GGG AAG TTT GAC ATC ATC CCT ACA ATG ACC ACC ATC GGC 1181
 317  I   L   V   D   G   K   A   G   K   F   D   I   I   P   T   M   T   T   I   G   336

1182 TCT GGA ATT GGC ATC TTT GGG GTG GCC ACA GTT CTC TGT GAC CTG CTG CTT CAC ATC 1241
 337  S   G   I   G   I   F   G   V   A   T   V   L   C   D   L   L   L   H   I   356

1242 CTG CCT AAG AGG CAC TAC TAC AAG CAG AAG TTC AAA TAC GCT GAG GAC ATG GGG CCA 1301
 357  L   P   K   R   H   Y   Y   K   Q   K   F   K   Y   A   E   D   M   G   P   376

1302 GGG GCG GCT GAG CGT GAC CTC GCA GCT ACC AGC TCC ACC AGC CTG GGC CTG CAG GAG AAC ATG 1361
 377  G   A   A   E   R   D   L   A   A   T   S   S   T   S   L   G   L   Q   E   N   M   396

1362 AGG ACA TCC TGA tgctcggccccaactcctgactggtgcagcgtgaggcttcagcctggagccctggtgggtcc 1437
 397  R   T   S   *                                                                   400

1438 cagccagggcagagggcctcccccaggaagtctcctccctctcagccaggcagagagcagttgcagaagctcagggt 1517

1518 gcatagtaggagagagacctgtgcaaatctgagctccggctccgaccccacacacaccctgagggaggctaccctagcttcag 1597

1598 ccgctccctggtggggaatggctgggggttgggcaggaccctccagcttccgtgcttctctcc 1677

1678 ggactctcattatccaaccgctgcctccattcctctagatctgtgctctccgatgtggcagtcagtaaccataggtgac 1757

1758 taaattaaactaaaataaatagaatgaaacacaaaattcaattcctcgctgaactagccacattcaactgctcagta 1837
```

Fig. 4D

```
1838  gatacgtgtggttagtggctgctgccatactggacagctcggggcattttcactgtcaaagaaagttctattagacagcccctg  1917
1918  cttgagccctgttttcttcctggcttcgtttccctggggaacttatcgacaatgcaagctcctggcccaccccagacc  1997
1998  tcctgaaccaaaagctccagggctggccgtatgatctgtggatggcaaactcccaggccattctggacctaagttt  2077
2078  aagaagtgccgtcctcgaactttctgactctaagctcctgagcgggagtcagactcagccctgagcctgcacttcctgtt  2157
2158  caggtgcagacactgaacagggtctcaaacaccttcagcatgtgtgttgctcacgtgccacacagtgtctcatgca  2237
2238  cacaacccagtgtacacaccactctacacccctccacactgtcgtgccatgtccgtgccatgtcacctcagggaaaggcttctc  2317
2318  acaaccatctacacacatctacacaccccagcacacacatgttccgtgccatgtccgtgccatgtcacctcagggaaaggcttctc  2397
2398  tccaagtgtgccaggacagcccctccagccatgaatcctactcagctacctcgggttgggtgggagcccagc  2477
2478  caaatccctggcctccctgcctgtggctcagcccagctcccaaggcctgcctctgtctgaacagaggtctgggg  2557
2558  aagcgaggggtggagtacaataaagggaatgaggacaaacaaaaaaaaaaaaaaaaaaaaaaa  2637
2638  aaaaaa  2643
```

Fig. 5

```
                    TM-1
Human  MARRF QEELAAFL FEYDTPRMVLVRNKKVGVIFRLIQLVVLVYVIGWVF L     50
Rat    MARRL QDELSAFF FEYDTPRMVLVRNKKVGVIFRLIQLVVLVYVIGWVF V Human  YEKGYQTSS GLISSVSVKLKGLAVTQL P GLGPQVWDVADYVFPA Q GDNSF    100
Rat    YEKGYQTSS DLISSVSVKLKGLAVTQL Q GLGPQVWDVADYVFPA H GDSSF
                                                        o
Human  VVMTNFIVTP K QTQG Y CAEH PEGGI C KEDSGCTPGKA K RKAQGIRTG K CV  150
Rat    VVMTNFIVTP Q QTQGH CAEN PEGGI Q DDSGCTPGKA E RKAQGIRTG N CV
                  *
Human  A FN DTVKTCEIFGWCPVEVDD I R PALLREAENFTLFIKNSISFPRFKV      200
Rat    P FN GTVKTCEIFGWCPVEVDD K I PS PALLREAENFTLFIKNSISFPRFKV
         o
Human  NRRNLVEEVN A AHM K T CLF HKTL HPLCPVF Q LGYVV Q ESG Q N FST LAEKG  250
Rat    NRRNLVEEVN GTY M KK CLY HKIQ HPLCPVF N LGYVV R ESG Q DFR S LAEKG
                                                              *
Human  GVVGITIDW H CDLDWHVRH C RPIYE FHGLY E EKNLSPGFNFRFARHFV EN    300
Rat    GVVGITIDW K CDLDWHVRH CK PIYQ FHGLY G EKNLSPGFNFRFARHFV QN
                                                             TM-2
Human  GTN Y RHLFKVFGI R FDILVDGKAGKFDIIPTMTTIGSGIGIFGVATVLCD    350
Rat    GTN R RHLFKVFGI H FDILVDGKAGKFDIIPTMTTIGSGIGIFGVATVLCD Human  LLLHILPKRHYYKQKKFKYAEDMGPGA A ER D LA ATSSTLGLQENMRTS*     400
Rat    LLLHILPKRHYYKQKKFKYAEDMGPG EGEH DP V ATSSTLGLQENMRTS*
```

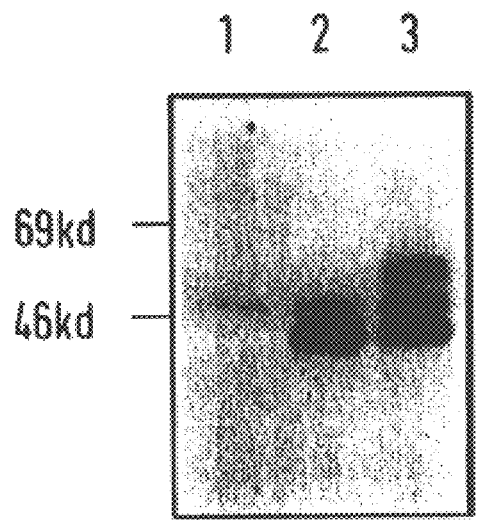
Fig. 6
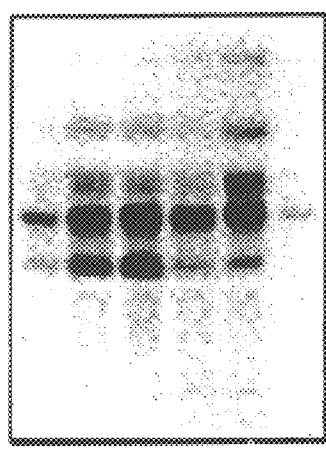
Fig. 7
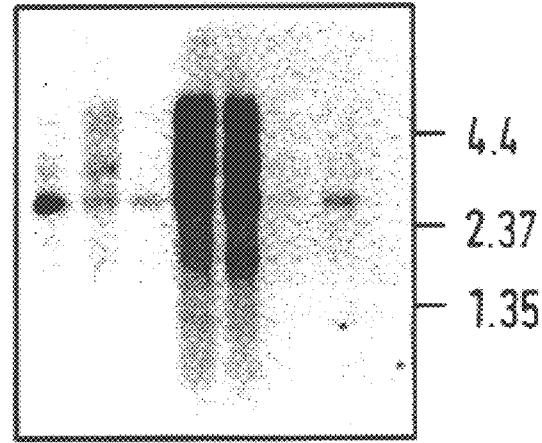
Fig. 8

$P_{2X}$ RECEPTOR DNA AND PROTEIN SEQUENCE

This invention relates to the $P_2X$-purinoceptor, its preparation and uses.

The $P_2X$-purinoceptor is a ligand-gated ion channel; that is, the receptor itself forms an ion channel which opens when extracellular adenosine 5'-triphosphate (ATP) binds to the receptor. There are five other classes of neurotransmitter receptors (nicotinic acetylcholine, glutamate, glycine, $GABA_A$ and $5-HT_3$); these form a structurally related superfamily of ligand-gated ion channels (Barnard, *Trends Biochem. Sci.* 17, 368–374, (1992)). The $P_{2X}$-receptor now identifies a new family of this type of receptor. The unique structure of this receptor, the widespread distribution of this receptor throughout the body, and the numerous physiological roles this receptor may play, make it an important protein that can be used to identify new, therapeutically effective, compounds for the treatment of a number of pathological states.

In 1929 the eminent physiologist Szent-Gyorgyi described powerful cardiovascular actions of extracellular purine nucleosides (e.g. adenosine) and nucleotides (e.g. ATP) (Drury & Szent-Gyorgyi, *J. Physiol.* 68 213–237 (1929)), but it was not until 1972 that pharmacological evidence was provided to suggest the existence of distinct receptors for extracellular ATP (ie. that recognise ATP but not adenosine) (Burnstock, *Pharmacological Reviews* 21 509–581 (1972)). The seminal and subsequent work on this area by Burnstock and colleagues was largely unaccepted throughout the 1970s and early 1980s until the development of a range of relatively selective ligands and techniques for directly measuring ATP release overwhelmingly substantiated Burnstock's hypothesis (Barnard et al., *Trends Pharmacol. Sci.* 15 67–70 (1994)). In the past four or five years, unequivocal evidence for the role of ATP as a neurotransmitter has been provided for sympathetic control of blood flow to the intestine and smooth muscle tone (contractility) in genitourinary tissue such as vas deferens, bladder and ureter (Barnard et al. (loc. cit.) and Evans & Surprenant, *Brit. J. Pharmacol.* 106 242–249 (1992)). Substantial indirect evidence also exists for the role of ATP as a neurotransmitter in a number of distinct neurones in the spinal cord, autonomic ganglia and certain nuclei in the central nervous system (Bean, *Trends Pharmacol. Sci.* 15 67–70 (1992), Evans et al., *Nature* 357, 503–505 (1992) and Edwards et al., *Nature* 359 144–147 (1992)).

Purinoceptors are classified as $P_1$ (adenosine as ligand) and $P_2$ (ATP as ligand). The $P_2$ receptors are subclassified into two broad types—those that are 7-transmembrane receptors that couple to G-proteins ($P_{2Y}$, $P_{2U}$, $P_{2T}$, and perhaps $P_{2Z}$) and those that form a directly gated ion channel ($P_{2X}$). Pharmacological and/or physiological evidence for subtypes of each of these types of receptors exists. The most recent nomenclature for these receptors is shown below.

|  | $P_{2X}$ | $P_{2Y}$ | $P_{2Z}$ |
|---|---|---|---|
| Type | Ligand-gated channel | G-protein coupled | Non-selective pore |
| Subtype | $P_{2X1}$, $P_{2X2}$, $P_{2X3}$ | $P_{2Y1}$, $P_{2Y2}$, $P_{2Y3}$ | |

Various $P_2$ receptors have previously been cloned. $P_{2Y1}$ was cloned by the Barnard/Burnstock group (Webb et al., *FEBS Lett.* 324 219–225 (1993)) based on homology with other 7-TM G-protein coupled receptors. This group used PCR technology and primers based on conserved domains of the second and sixth transmembrane regions to screen a mammalian brain cDNA library and, with final success, an embryonic chick whole-brain cDNA library.

$P_{2Y2}/P_{2U}$ was cloned by the Julius laboratory (Lustig et al., *Proc. Nat'l. Acad. Sci. USA* 90 5113–5117 (1993)) by expression cloning in the oocyte from cDNA obtained from a NG108-15 neuroblastoma cell line.

$P_{2Y3}/P_{2T}$ was also obtained by the Barnard/Burnstock group using the same probes and embryonic brain cDNA library used to obtain the $P_2Y1$ receptor (Barnard et al., *Trends Pharmacol. Sci.* 15 67–70 (1994)).

However, as yet, cloning of the $P_{2X}$ receptor has remained an elusive goal. The prior cloning exercises undertaken for the other $P_2$ receptors do not provide an adequate lead to enable the $P_{2X}$ receptor to be cloned. First, all the above purinoceptors are G-protein coupled 7-TM proteins. Their myriad functions (like those of all 7-TM receptors) occur through G-protein activation of one or more second messenger systems. There are over 200 currently identified proteins which belong to this 7-TM/G-protein coupled family. Agonists at these receptors activate cascades of intracellular transduction pathways, often involving several enzymes; the response of the cell is inherently slow (several seconds to minutes) and changes in excitability are subtle if they occur. In contrast, the $P_{2X}$ receptor is a fundamentally different type of purinoceptor that incorporates an ion channel. Activation of $P_{2X}$ receptors is rapid (milliseconds), has predominately local effects, and brings about immediate depolarisation and excitation.

Secondly, the tissue distribution of the $P_{2X}$ receptor is distinctly different from other purinoceptors, and the physiological roles differ from other purinoceptors.

One of the principal established ways to clone a receptor is based on sequence relatedness of the nucleotides that encode the amino acids of the receptor protein; it depends on there being a fairly high level of homology between a known sequence and that of the unknown receptor. This method was used to clone the $P_{2Y1}$ form (above). Several laboratories, including that of the applicants, invested significant effort in obtaining the $P_{2X}$ receptor using PCR techniques and primers based on conserved regions of various ligand-gated ion channels (ie. nicotinic ACh, GABA, glutamate, $5-HT_3$). This approach failed. With hindsight, this failure can be rationalised, as it can now, but only now, be seen that the structure of the $P_{2X}$ receptor bears no homology with any of these ligand-gated ion channels. For the same reason, approaches based on fragment hybridisation would not succeed.

However, by adopting a different approach, it has now been found possible to clone the $P_{2X}$ receptor, and it is on this achievement that the present invention is in part based.

According to a principal aspect of the present invention, there is provided a recombinant or isolated DNA molecule encoding a $P_{2X}$ receptor, wherein the receptor:

(a) has the amino sequence shown in FIG. 1, FIG. 2, FIG. 3 or FIG. 4; or (b) is substantially homologous to the sequence shown in FIG. 1, FIG. 2, FIG. 3 or FIG. 4;

or a fragment of such a DNA molecule, which fragment includes at least 15 nucleotides taken from nucleotides 1 to 813 shown in FIG. 1, the full nucleotide sequences shown in FIGS. 2 and 3, or from nucleotides 1 to 1744 shown in FIG. 4.

The sequence shown in FIG. 1 is a cDNA sequence that encodes a rat vas deferens $P_{2X}$ receptor. This sequence is 1837 bases in length and encodes a protein of 399 amino acids. As was determined after the receptor was cloned, approximately one half of the protein-encoding sequence, from nucleotides 814 onwards, had been discovered previously but the function of the previously cloned sequence was not known except that it appeared to be implicated in apoptotic cell death (Owens et al., *Mol. Cell. Biol.* 11 4177–4188 (1991)); the Owens et al sequence lacks a translation initiation site and could not be made into protein. (In FIG. 1, the upstream portion of the reported sequence of Owens et al., namely PQLAHGCYPCPPHR, which is not shared with the $P_{2X}$ receptor, is shown for comparative purposes and does not form part of the invention.)

Preferably the FIG. 1 sequence fragments are taken from nucleotides 1–810. Often the FIG. 4 sequence fragments are taken from nucleotides 1–777.

The sequence shown in FIG. 2 is a cDNA sequence that encodes a rat superior cervical ganglion $P_{2X}$ receptor.

The sequence shown in FIG. 3 is a cDNA sequence that encodes a rat dorsal root ganglion $P_{2X}$ receptor.

The sequence shown in FIG. 4 is the cDNA sequence that encodes a human $P_{2X}$ receptor. The cDNA was isolated from the human urinary bladder using a rat $P_{2X}$ probe. It is 2643 bases long and encodes a 399 amino acid protein having an amino acid sequence which is highly homologous with the amino acid sequence of the rat $P_{2X}$ receptor isolated from rat vas deferens and with the rat $P_{2X}$ receptors isolated from a rat superior cervical ganglion and from a rat dorsal root ganglion. Recently we have become aware of an expressed sequence tag corresponding to residues 1745–1933 (Proc. Natl. Acad.Sci. USA 91,10645–10649 (Oct. 1994).

Sequences which are substantially homologous to the FIG. 1, FIG. 2, FIG. 3 or FIG. 4 amino acid sequence include those which encode proteins having at least 40%, 50%, 60%, 70%, 80%, 90%, 95% or 99% homology in increasing order of preference. A protein having at least 99% homology with the amino acid sequence of FIG. 1, FIG. 2, FIG. 3 or FIG. 4 will have no more than four amino acid variations from such a sequence. Preferred substantially homologous sequences include $P_{2X}$ sequences from other species. Thus for the rat $P_{2X}$ receptor sequences a preferred substantially homologous sequence is a human $P_{2X}$ sequence. One method of determining sequence homology is disclosed in W R Pearson and D J Lipman, *Proc Natl Acad Sci USA* 85:2444–2448 (1988).

Fragments may of course be larger than 15 nucleotides. Fragments encoding substantially the whole of the $P_{2X}$ rat receptors or human receptor may be expected to share the biological activity of the receptor, or at least some of its biological activities. Shorter fragments may be useful for encoding one or more selected domains of the receptor, or simply as probes for detecting or identifying other useful DNA sequences, including those encoding substantially homologous proteins. Fragments of at least 20, 30 or 50 nucleotides may be more frequently of use than shorter ones.

DNA molecules of the invention are useful for a number of purposes. First, and not least, the $P_{2X}$ cDNA shown in FIG. 1, in FIG. 2, in FIG. 3 and in FIG. 4 enables the relevant proteins to be expressed in living cells. This would not be possible with fragments of the cDNA. However not only are fragments of DNA within the scope of the invention, for the various purposes mentioned above, but also genomic and other sequences of DNA (including synthetic DNA and "minigenes", which include at least one, but not all, of the introns naturally present in the gene) are included within its scope. cDNA sequences encoding the rat receptor proteins or human $P_{2X}$ receptor protein may be preferred in some circumstances because such sequences are smaller than either genomic or minigene DNA and therefore more amenable to cloning manipulations. The $P_{2X}$ receptor protein can be stably expressible in chinese hamster ovary (CHO) cells, as will be described below.

Still on the subject of expression, while it would be possible to express genomic DNA in eukaryotic cells, it is much more difficult to manipulate the DNA for insertion into host cells due to the larger size that commonly results from introns. The size is particularly important for the expression of RNA; very long cRNAs—the size of whole genes—are difficult to make in sufficient quantity. On the other hand, expression from RNA is much preferred at least for the investigation of ion channel proteins, because the Xenopus oocyte is sufficiently large to be studied easily by electrophysiological methods.

Secondly, the cDNA sequences encode proteins that, in their predicted folding within the membrane, differ from other known proteins. This is advantageous because, based on historical precedent, this will lead to the discovery of a large family of related proteins and these may have functional roles unrelated to signalling mediated by ATP.

Thirdly, knowledge of the protein sequences encoded by rat and human $P_{2X}$ cDNA allows the development of molecular models that predict the detailed disposition within the membrane. It further allows the correctness of such models to be determined by expression of mutagenised proteins. These two approaches are advantageous because they may permit the molecular design of complementary therapeutic agents that activate or block the receptor.

Fourthly, the $P_{2X}$ cDNA sequences allow the distribution of the RNA that encodes this receptor, as well as the receptor protein itself, to be mapped in human tissues. RNA distribution can be determined by in situ hybridisation. Such hybridisation studies are disclosed in the present examples. Knowledge of a deduced amino acid sequence from cDNA allows synthetic peptides to be made that can be used to generate antibodies that selectively recognise a $P_{2X}$ receptor. Thus a $P_{2X}$ protein can be mapped by immunohistochemistry. This may suggest novel therapeutic applications for drugs that activate or block the $P_{2X}$ receptor, that can not be predicted on the basis of less sensitive current methods for localising the receptor (radioactive ligand binding).

Fifthly, rat $P_{2X}$ cDNA is advantageous because it can allow the isolation of a closely related cDNA from human tissue.

Sixthly, the isolation of the human $P_{2X}$ cDNA clone will enable a human genomic clone to be obtained. It is probable that mutations of this gene will be discovered that lead to human genetic disease. The analysis of such mutations may lead to appropriate treatments of diseases or disorders caused by such mutations.

In one aspect of the present invention rat vas deferens $P_{2X}$ receptor was cloned by a method which does not require prior inference about structure. Tissues were chosen that were believed to be rich in the RNA for the receptor of interest. A number of tissue sources were tried but they did not provide RNA that led to ATP responses in oocytes. Eventually, vas deferens was chosen. From extracted polyadenylated RNA, a cDNA library or bank that corresponds as far as possible to the DNAs in the tissue was constructed. It was not assured, either before work began or until it was satisfactorily completed, that a satisfactory cDNA library in which the rat $P_{2X}$ gene was represented could be constructed; nevertheless, this was achieved in plasmid pBKCMV.

An individual clone within the library that contains the rat vas deferens $P_{2X}$ cDNA of interest was detected by progressive fractionation of the library; at each step the fraction was tested to determine whether RNA made from it can direct the formation of the protein of interest. More specifically, RNA was transcribed in vitro from the cDNAs in the library (approximately 2 million) and the RNA ("cRNA") mixture was injected into immature Xenopus oocytes. cRNA is very susceptible to inadvertent enzymatic degradation, so all procedures were carried out under sterile conditions. The cDNA pools were made by the miniprep procedure and therefore contained large amounts of E. coli RNA; this difficulty was overcome by precipitating any RNA before the cRNA was transcribed.

Detection of the protein can in principle be done by radioactive ligand binding or by a functional response. The activation of G proteins in the Xenopus oocyte and the subsequent cellular response was used to obtain the $P_{2Y2}/P_{2U}$ receptor. In the present work, a decision was made to use the opening of the integral ion channel of the $P_{2X}$ as the response. Individual oocytes were screened two days after injection to determine whether they had made $P_{2X}$ receptor protein in their membrane. This was done by recording the current flowing across the oocyte membrane when ATP (30 $\mu$M) was applied to the outside of the oocyte; if the $P_{2X}$ receptor has been produced, a small transient current would be expected. However, testing for expression of the receptor was not straightforward, as some batches of oocytes exhibit responses to ATP because they naturally express other kinds of ATP receptor. This difficulty was overcome as follows: when an oocyte responded to ATP with the expected current this was further tested by blockade with a $P_{2X}$ receptor antagonist (suramin). The cDNA fraction that gave led to the positive response in such an oocyte was further divided, and each fraction was again tested. Such progressive fractionation led to isolation of a single clone. The insert in the plasmid was sequenced; the sequence is shown in FIG. 1. This sequence was used to design PCR primers which were used in the cloning of cDNA encoding a $P_{2X}$ receptor from a rat superior cervical ganglion (see FIG. 2). A similar procedure was then used in the cloning of cDNA encoding a $P_{2X}$ receptor from a rat dorsal root ganglion (see FIG. 3).

DNA in accordance with the invention will usually be in recombinant or isolated form and may be in the form of a vector, such as a plasmid, phagemid, cosmid or virus, and in some embodiments contains elements to direct expression of the protein, for example in a heterologous host. Non-expressible vectors are useful as cloning vectors.

Although DNA in accordance with the invention may be prepared synthetically, it is preferred that it be prepared by recombinant DNA technology. Ultimately, both techniques depend on the linkage of successive nucleotides and/or the ligation of oligo- and/or poly-nucleotides.

The invention enables, for the first time, $P_{2X}$ receptor to be prepared by recombinant DNA technology and hence free from protein with which it is naturally associated or contaminated (such as the $P_{2U}$ or, particularly, $P_{2Y}$ receptor, or other ATP receptors or binding proteins), and this in itself forms another aspect of the invention. The protein will generally be associated with a lipid bilayer, such as a cell, organelle or artificial membrane. $P_{2X}$ receptor prepared by expression of DNA in accordance with the first aspect may be glycosylated, but does not have to be. Generally speaking, receptor proteins and ion channels that are glycosylated will also function after carbohydrate removal or when expressed in cells that do not glycosylate the protein. However, there are often important quantitative differences in the function between the glycosylated and non-glycosylated protein. In the case of the rat vas deferens $P_{2X}$ receptor, we believe that the native protein is glycosylated because it has a molecular weight of 62 kd when purified from the rat vas deferens, as compared to the molecular weight of 45 kd for the cloned protein. Similar results were obtained for the human $P_{2X}$ receptor (see later).

There are also several asparagine residues in the extracellular domain that are likely sites of sugar attachment.

Knowledge of the amino acid sequence of a $P_{2X}$ receptor enables the protein or peptide fragments of it to be prepared by chemical synthesis, if required. However, preparation by expression from DNA, or at least translation from RNA, will usually be preferred.

Particularly useful peptide fragments within the scope of the invention include epitopes (which may contain at least 5, 6, 7, 10, 15 or 20 amino acid residues) of the $P_{2X}$ receptor which are immunologically non-cross reactive with the RP-2 polypeptide disclosed in Owens et al., loc. cit.

A $P_{2X}$ receptor, and fragments of it, can be used to prepare specific polyclonal and monoclonal antibodies, which themselves form part of the invention. Polyclonal and monoclonal antibodies may be prepared by methods well established in the art. Hybridoma and other cells expressing monoclonal antibodies are also within the invention.

RNA encoding a $P_{2X}$ receptor, transcribable from DNA in accordance with the invention and substantially free form other RNAs, also forms part of the invention, and may be useful for a number of purposes including hybridisation studies, in vitro translation and translation in appropriate in vivo systems such as Xenopus oocytes.

The invention also relates to host cells transformed or transfected with a vector as described above. Host cells may be prokaryotic or eukaryotic and include mammalian cells (such as COS, CHO cells and human embryonic kidney cells (HEK 293 cells)), insect cells, yeasts (such as Saccharomyces cerevisiae) and bacteria (such as Escherichia coli). Host cells may only give transient expression of the receptor, as in the case of COS cells, but for preference the host cells are stably transfected with the vector. Host cells which appropriately glycosylate the receptor are preferred. A CHO cell line or any other cell line that stably expresses a $P_{2X}$ receptor can be used for electrophysiological, calcium-influx, calcium-imaging and ligand-binding studies. Host cells which do not express the receptor may still be useful as cloning hosts.

A $P_{2X}$ receptor prepared by recombinant DNA technology in accordance with the invention has a number of uses, either in situ in a membrane of the expression host or in in vitro systems. In particular, the receptor can be used as a screen for compounds useful in a variety of human (or other animal) diseases and conditions, as will now be briefly described. Such compounds include those present in combinatorial libraries, and extracts containing unknown compounds (e.g. plant extracts).

Epilepsy

Epilepsy results from overexcitation of distinct neurones in specific regions of the brain, in particular in the hippocampus. Functional ATP $P_{2X}$ receptors are known to be present in some hippocampal neurones. If the $P_{2X}$ receptors are expressed on inhibitory interneurons, then receptor agonists would be therapeutically useful. If the receptor is expressed on principal (pyramidal or granule) cells, then receptor antagonists will be useful. If will now be possible to determine which classes of neuron express the receptor.

Cognition

Hippocampal neurones respond to ATP by activation of a $P_{2X}$ receptor; these areas are of primary importance to cognition. It is now possible to determine the cellular localisation of the $P_{2X}$ receptor with in the hippocampus; depending on this localisation, either agonists or antagonists might be effective to enhance memory.

Emesis

The acute trigger for emesis is rapid contraction of smooth muscle of the upper gastrointestinal tract. Activation of ATP $P_{2X}$ receptors present on smooth muscle of the GI tract, in particular the stomach and trachea, results in strong, rapid muscle contractions. $P_{2X}$-antagonists selective for visceral smooth muscle could be useful for emesis. Furthermore, $P_{2X}$ receptors are known to be expressed in the nucleus of the tractus solitarius (Ueno et al., *J. Neurophysiol.* 68 778–785 (1992)) and may be involved in transmission from primary visceral afferents; this could be blocked by selective $P_{2X}$ antagonists.

Pain

First, $P_{2X}$ receptors are expressed in dorsal horn neurones of the spinal cord. Activation of these neurones by ATP causes fast depolarizing, excitatory responses (Jahr & Jessell, *Nature* 304 730–733 (1983)); if a component of the transmission from nociceptive fibres is mediated by ATP then this could be blocked by a $P_{2X}$ antagonist. Secondly, ATP is one of the most noxious substance known when applied intradermally. This is because it activates directly the peripheral terminals of small diameter nociceptive fibres; it is known that the cell bodies in the dorsal root ganglion express $P_{2X}$ receptors. A $P_{2X}$ antagonist would be a peripherally active analgesic, and is likely to be effective in migraine.

Asthma

Bronchial smooth muscles contract in response to activation of $P_{2X}$ receptors. This may occur in response to ATP released from sympathetic nerves, or from local immune cells. $P_{2X}$ antagonists may help to prevent stimulus-evoked spasms of bronchial smooth muscle and thereby reduce the frequency and/or severity of asthmatic attacks.

Peripheral vascular disease

It is becoming clear that ATP and not noradrenaline is the primary vasoconstrictor neurotransmitter in small resistance arteries—those that comprise over 70% of total peripheral resistance. This has been shown for many vessels (Westfall et al., *Ann. N.Y. Acad. Sci.* 603 300–310 (1991)). A selective antagonist could be used for local collateral vaso-dilation.

Hypertension

Hypertension that is associated with increased sympathetic tone could be treated with $P_{2X}$ receptor antagonists, because ATP is a major excitatory transmitter to many resistance vessels in several species including man (Westfall et al., loc. cit. and Martin et al., *Br. J. Pharmacol.* 102 645–650 (1991)).

Diseases of the immune system

A molecule identical to part of the $P_{2X}$ receptor has been cloned from thymocytes that have been induced to die (Owens et al., loc. cit.).

The selective expression in these conditions implies that a molecule closely related to the $P_{2X}$ receptor plays a role in the apoptosis that is an integral part of the selection of immunocompetent cells. The molecule described by Owens et al. (RP-2) was incomplete and could not have been translated into protein. The cloning of the $P_{2X}$ receptor will now allow the isolation of full length RP-2 clones, their heterologous expression and the determination of their functional roles.

Irritable bowel syndrome

ATP is an important transmitter to the smooth muscles of the intestinal tract, particularly in the colon. It is also a transmitter between neurons in the enteric nervous system, by activating $P_{2X}$ receptors (Galligan, *Gastroenterology*, in press). Antagonists at $P_{2X}$ receptors may therefore have utility in the management of this condition.

Premature ejaculation

This could be prevented by preventing stimulus-evoked contraction of vas deferens smooth muscle. $P_{2X}$ receptors are highly expressed in this tissue; antagonists at this site would prevent vas deferens contractility during sympathetic excitation.

Cystitis $P_{2X}$ receptors may be implicated in increased bladder sensitivity in patients with cystitis. Thus antagonists of such $P_{2X}$ receptors may be useful in treating cystitis.

Useful agonists and antagonists identified as described above also form an aspect of the invention.

The cloning of the $hP_{2X}$ receptor is an important aspect of the present invention. $hP_{2X}$ is the first human member of a multigene family of ionotropic purinoceptors. Its strong similarity with $P_{2X}$, isolated from rat vas deferens and with $P_{2X}$ isolated from rat superior cervical ganglion or from rat dorsal root ganglion, suggests that it is a human homolog of the rat proteins. The present inventors have found that differences between these two sequences are nearly all conservative substitutions of hydrophilic residues. Surprisingly, $hP_{2X}$ has only 41% identity with the other reported $P_{2X}$ receptor, that from rat PC12 cells (Brake et al, New structural motif for ligand-gated ion channels defined by an ionotropic ATP receptor *Nature* 371: 519–523 (1994)). The PC12 derived receptor was proposed to have a similar membrane topography and shares the conserved spacing of cysteine residues, indicated for the two smooth muscle sequences in FIG. 5.

The computed molecular weight of the $hP_{2X}$ polypeptide (45 kd) agrees with that of the in vitro translation product when made in absence of pancreatic microsomal membranes. A larger product, 60 kd, produced in presence of microsomes suggests glycosylation and supports the idea of a central extracellular domain. The predicted $hP_{2X}$ protein thus has the general features of other cloned members of this family (Valera et al, A new class of ligand-gated ion channel defined by $P_{2X}$ receptor for extracellular ATP *Nature* 371: 516–519 (1994); Brake—supra): a large, cysteine-rich extracellular central domain flanked by two transmembrane spans and short internal N- and C-termini.

The distribution of the $hP_{2X}$ mRNA was examined by northern blot analysis. Hybridisation of a principal 2.6 kb species was seen in all RNA samples tested, with the exception of brain. A smaller, 1.8 kb band, observed in spleen, and lung mRNAs could be due to a shorter 3' untranslated portion of the mRNA, as occurs for $P_{2X}$ mRNA from the rat vas deferens. The hybridisation observed in thymus, lung, spleen and liver RNA may reflect the content of smooth muscle in those organs. However, $hP_{2X}$ is likely to have roles in other cell types, as demonstrated by its presence in adrenal gland, and the hemopoetic cell line HL60. The strong induction of $hP_{2X}$ mRNA by HL60 differentiation may reflect a parallel observation in rat in which the smooth muscle form of $P_{2X}$ mRNA can be induced in immature thymocytes by dexamethasone ($RP_2$ mRNA; Owens et al, Identification of mRNAs associated with programmed cell death in immature thymocytes *J J Molec Cell Biol* 11: 4177–4188 (1991)).

The present invention has enabled the first comprehensive pharmacological characterization of a cloned $P_{2X}$-purinoceptor to be made. The time course of the responses to ATP and the sensitivity to $\alpha,\beta$,-methylene ATP are similar to those reported for the native $hP_{2X}$ in urinary bladder (Inoue & Brading, Human, pig and guinea-pig bladder smooth muscle cells generate similar inward currents in response to purinoceptor activation *Br J Pharmacol* 103:

1840–1841 (1991)). Thus the functional properties of some native $P_{2X}$ purinoceptors can be obtained by the expression of a single molecular species. The agonist induced current recorded from ooctyes expressing the $hP_{2X}$ clone gives a direct measure of the activation of $P_{2X}$-purinoceptors in a system with low levels of endogenous ectonucleotidase activity. The agonist profile 2MeSATP≧ATP>α,β,-meATP for $hP_{2X}$ is similar to that of the cloned rat vas deferens $P_{2X}$-purinoceptor. The high potency of α,β,-meATP in whole tissue studies (α,β,-meATP >>2MeSATP≧ATP) probably reflects, its resistance to ectonucleotidases.

The concentration-effect curves for ATP, 2MeSATP and 2-chloro-ATP were superimposable, indicating that these particular substitutions at the 2' position on the adenine ring do not affect agonist binding to the $P_{2X}$-purinoceptor. The agonist activity of $AP_5A$ is likely to be because diadenosine phosphates ($AP_5A$, and $AP_6A$) released from the platelets can act as vasoactive agents through activation of $P_{2X}$-purinoceptors.

Preferred features of each aspect of the invention are as for each other aspect, mutatis mutandis.

BRIEF DESCRIPTION OF THE DRAWINGS

The invention will now be illustrated by the following examples. The examples refer to the accompanying drawings, in which:

FIGS. 1A–1C show DNA sequence (SEQ ID NO:4) and amino acid sequence (SEQ ID NO:5) of the rat vas deferens $P_{2X}$ receptor as determined in Example 2.

FIGS. 2A–2C show DNA sequence (SEQ ID NO:6) and amino acid sequence (SEQ ID NO:7) of a rat superior cervical ganglion $P_{2X}$ receptor, as determined in Example 11.

FIGS. 3A–3C show DNA sequence (SEQ ID NO:8) and amino acid sequence (SEQ ID NO:9) of a rat dorsal root ganglion $P_{2X}$ receptor, as determined in Example 12.

FIGS. 4A–4D show DNA sequence (SEQ ID NO:10) and amino acid sequence (SEQ ID NO:11) of a human $P_{2X}$ receptor as determined in Example 6.

FIG. 5 shows the alignment of the predicted amino acid sequence of $hP_{2X}$ (SEQ ID NO:11) with the rat vas deferens $P_{2X}$ (SEQ ID NO:5), and in vitro translation of $hP_{2X}$ protein.

Figure 9:
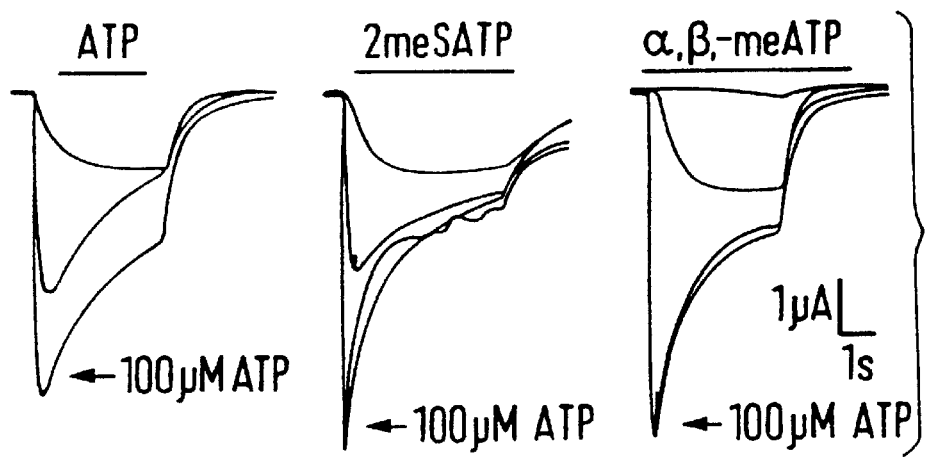

TM1 and TM2 filled boxes indicate the hydrophobic regions and boxed amino acids indicate the differences between the two sequences, o indicates conserved cysteine residues.

* Indicates potential sites of N-glycosylation.

FIG. 6 shows an SDS-PAGE analysis of $^{35}$S-methionine labelled $hP_{2X}$ protein. Lanes 1 and 2 show in vitro coupled transcription/translation of pBKCMV-$hP_{2X}$ cDNA in the absence and presence of microsomal membranes, respectively.

FIGS. 7 AND 8 show Northern analyses of the $hP_{2X}$ cDNA, wherein:

A) FIG. 7 shows Northern blot with 8 μg of total RNA from differentiated HL60 cells.

0 indicates HL60 cells without treatment;

PMA2 and PMA3 indicate respectively cells treated 2 days, and 3 days with PMA;

DMSO indicates cells treated 6 days with DMSO;

dcAMP indicates cells treated 5 days with dibutryl cAMP;

UB indicates 100 ng of polyA$^+$ RNA from human urinary bladder; and

B) FIG. 8 shows distribution of $hP_{2X}$ in human tissues. Lanes contained 1 μg polyA$^+$ RNA except for the urinary bladder which contained 0.2 μg of polyA$^+$ RNA.

Figure 10:
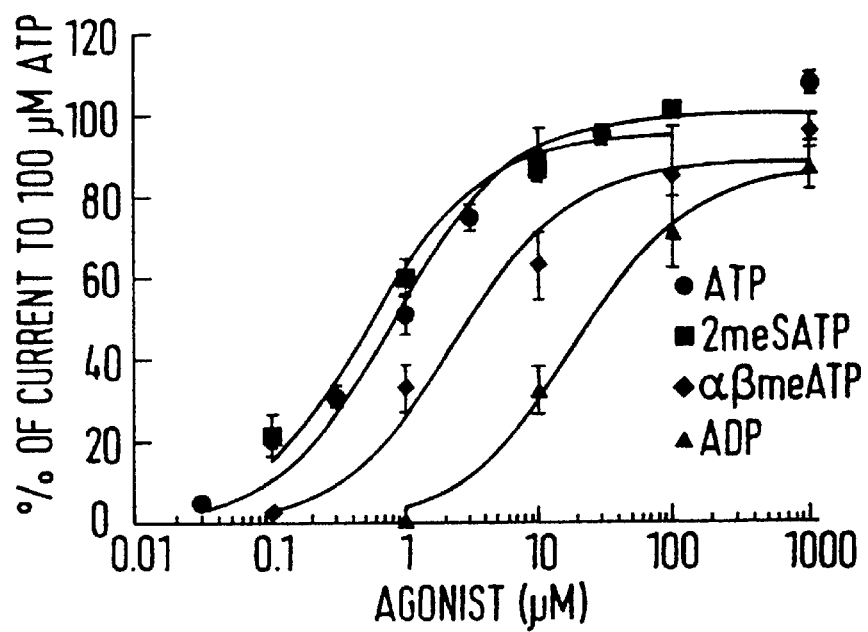
Figure 11:
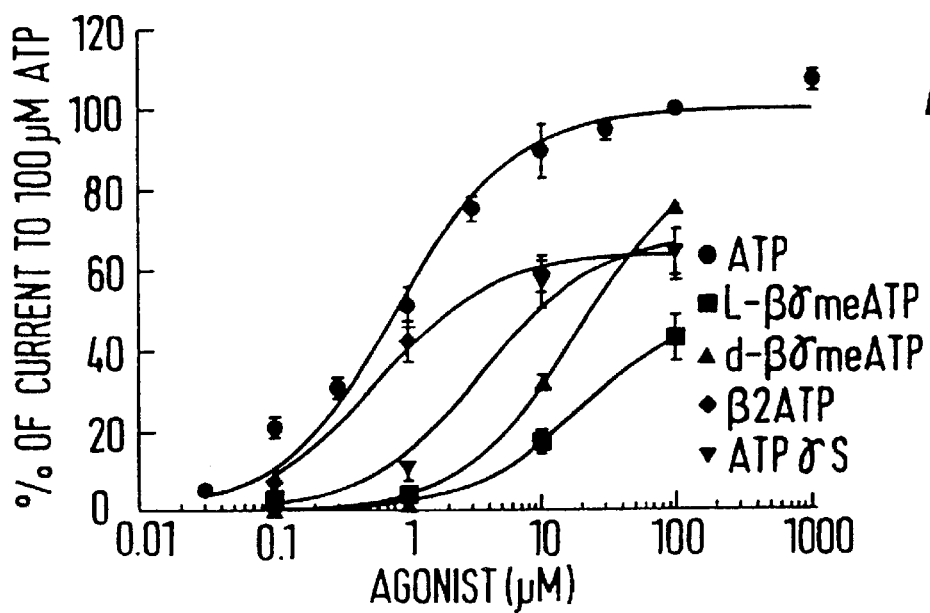

FIGS. 9, 10 and 11 show the response of oocytes expressing $hP_{2X}$ to purinoceptor agonists, wherein:

A) FIG. 9 shows traces which show inward currents evoked by ATP, 2 me SATP and α,β, me ATP (0.1, 1, and 100 μM). Records for each agonist are from separate oocytes;

B) FIG. 10 shows concentration response relationships of full $P_{2X}$-purinoceptor agonists. Data are expressed relative to the peak response to 100 μM ATP; and C) FIG. 11 shows concentration response of partial $P_{2X}$-purinoceptor agonists. Data are fitted with a Hill slope of 1 (n=4–8).

Figure 12:
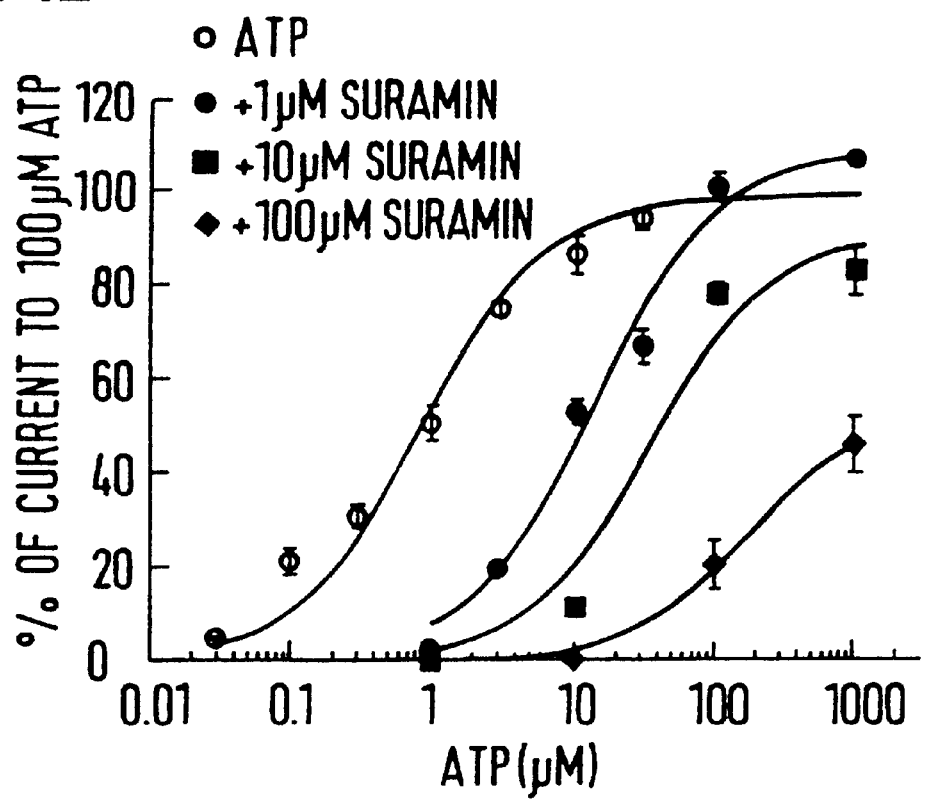
Figure 13:
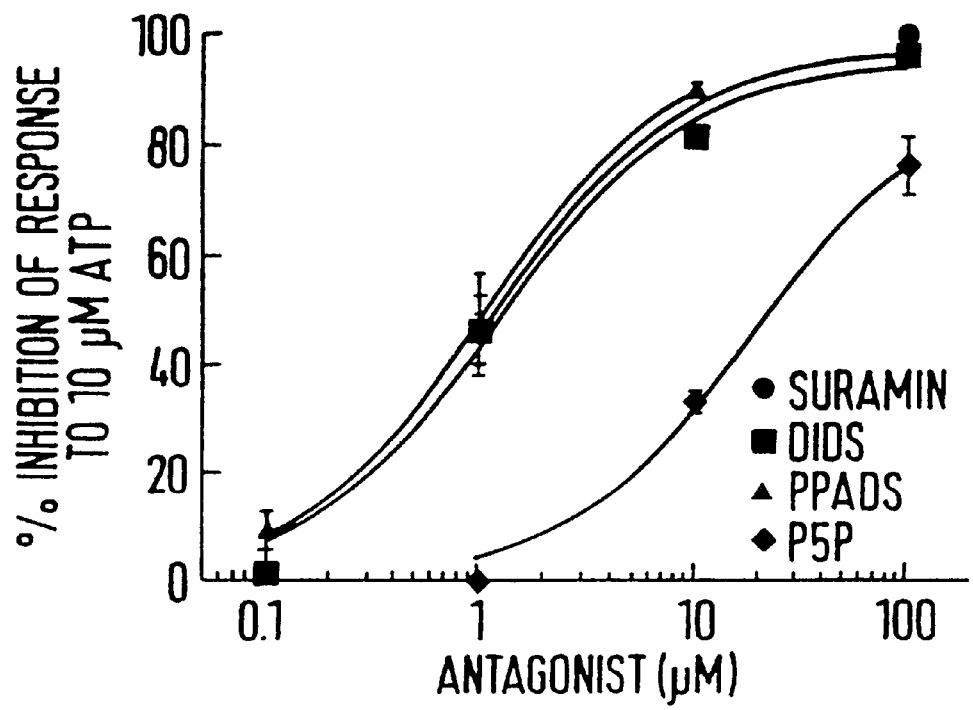
Figure 14B:
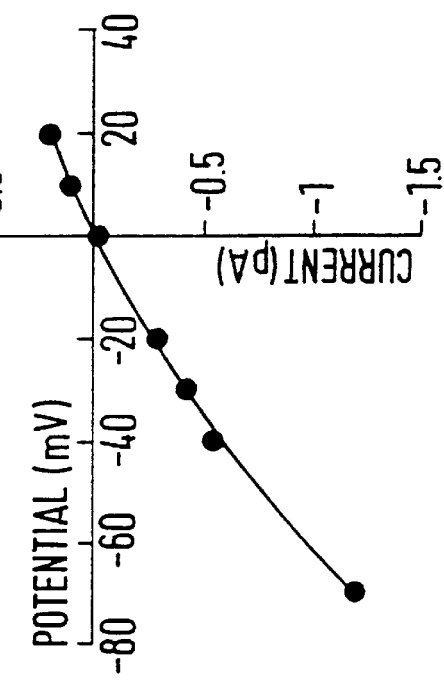
Figure 14D:
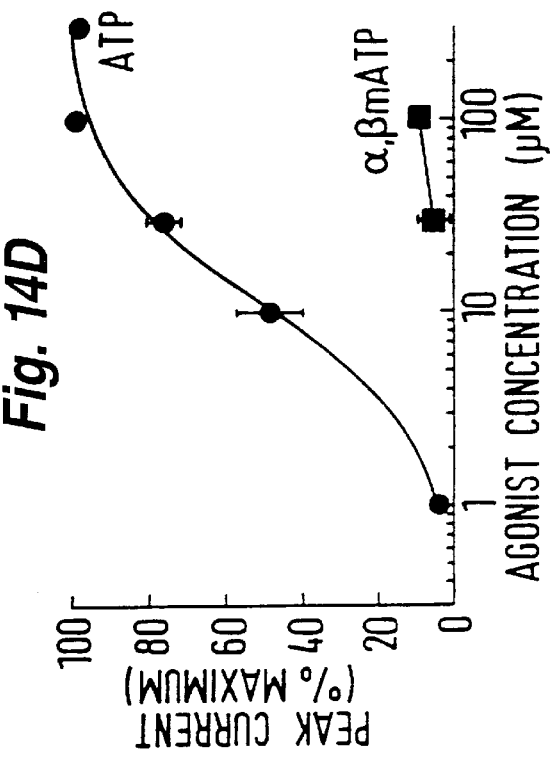
Figure 14A:
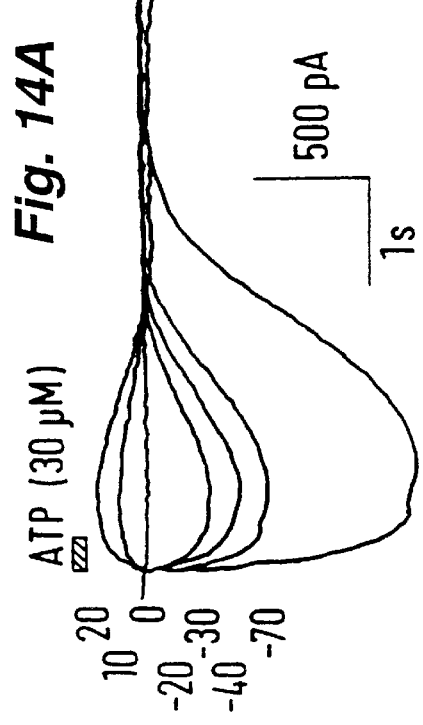
Figure 14C:
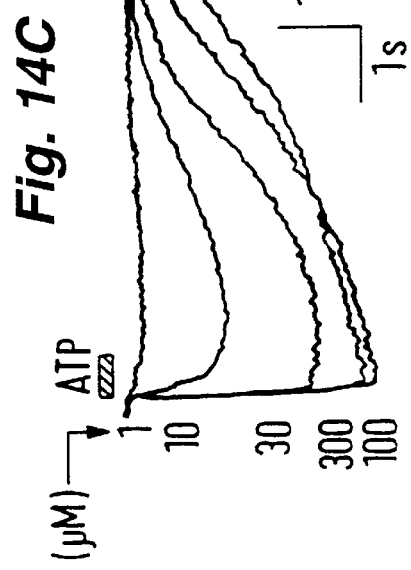

FIGS. 12 and 13 show the effects of $P_2$-purinoceptor antagonists of $hP_{2X}$ mediated responses, wherein;

A) FIG. 12 shows concentration response curves for ATP in the presence of the $P_2$-purinoceptor agonist suramin (1, 10 and 100 μM) (n=4 for each point); and B) FIG. 13 shows concentration dependence of suramin, DIDS, PPADS and $P_5P$ in inhibiting the response to 10 μM ATP (n=4 for each point).

FIGS. 14A–14D show the results of the functional characterisation of rat superior ganglion $P_{2X}$ receptors (as encoded by clone 3, described in Example 10). These experiments provided electrical recordings from transfected HEK293 cells.

Top left: Superimposed currents evoked by ATP (30 μM) during the time are indicated by the bar. Holding potential was changed from −70 to 20 mV.

Top right: Peak current as a function of membrane potential.

Bottom left: Superimposed currents evoked by ATP, from 1 to 300 μM.

Bottom right: Concentration-response curves for ATP and αβmethylene-ATP (points are mean ±s.e. mean for 5–8 experiments).

Figure 15A:
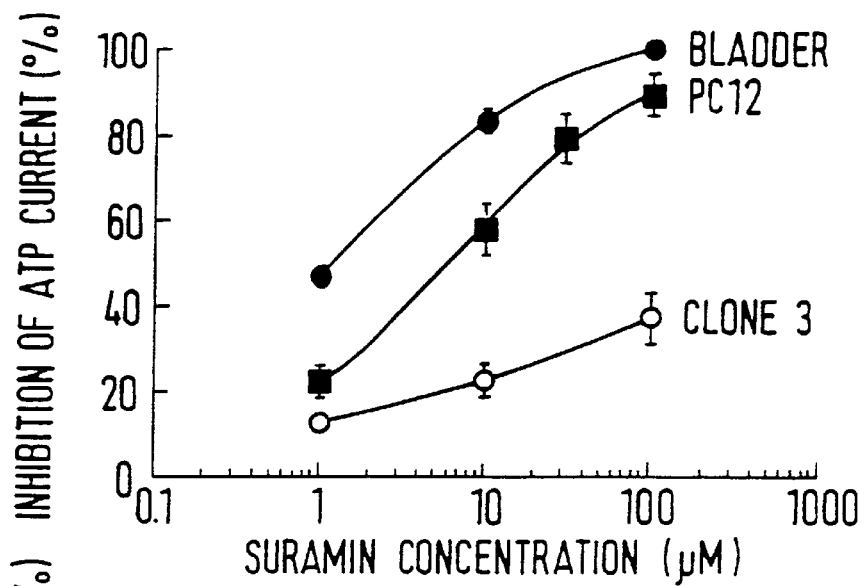
Figure 15B:
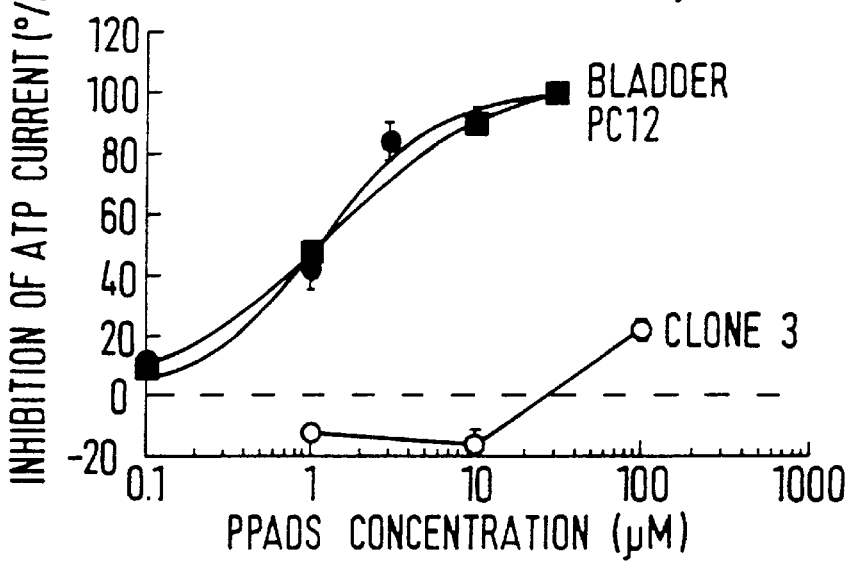
Figure 15C:
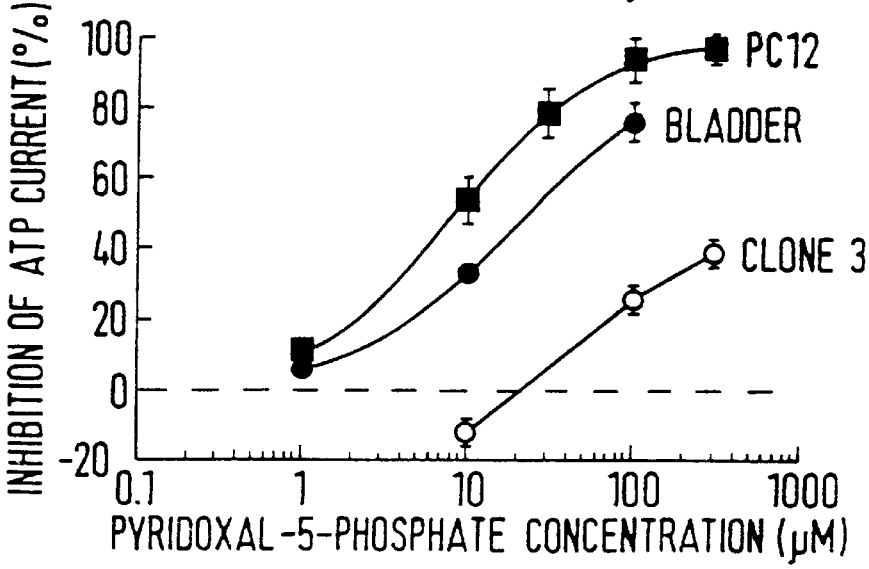

FIG. 15A–15C shows the inhibition of currents caused by various substances acting on the clone 3 form of the $P_{2X}$ receptor (as described in Example 11), compared with PC12 and human bladder forms in HEK293 cells.

Top: inhibition by suramin.

Middle: inhibition by PPADS.

Bottom: inhibition by pyridoxal 5-phosphate.

EXAMPLES (i) RAT VAS DEFERENS $P_{2X}$ RECEPTOR

EXAMPLE 1

Cloning of the Rat vas deferens $P_{2X}$ Receptor

Total RNA was isolated by the guanidinium isothiocyanate method (Sambrook et al., "Molecular Cloning: A Laboratory Manual" Cold Spring Harbor Laboratory Press, second edition (1989)) from vas deferens of 4 weeks old Sprague-Dawley male rats, and the poly A+ RNA was subsequently purified by oligo(dT)-cellulose. First strand cDNA primed with the sequence 5'-GAGAGAGAGAGCGGCCGCTTTTTTTTTTTTTT-3' (SEQ ID NO 1) was synthesised with SUPERSCRIPT™ (BRL, Gaithersburg, Md., USA) After conversion of the cDNA to double stranded (Gubler & Hoffman, Gene 25 263–269 (1983)) EcoRI linkers were ligated to the cDNA, and the product was digested with NotI. The EcoRI-NotI cDNA of 1.3 to 9 kb was isolated by gel electrophoresis, and a unidirectional library was constructed by ligation of the cDNA to PBKCMV (Stratagene, San Diego, Calif., USA) digested with the same enzymes. The library was electroporated into E. coli DH10B cells and divided in 24 pools of 8×10⁴ clones. The plasmid DNA from the pools was prepared by minialkaline lysis followed by LiCl precipitation (Sambrook et al., loc. cit). NotI-linearised cDNA was transcribed in vitro with T3 RNA polymerase in the presence of the cap analogue m7GpppG (Sambrook et al., loc. cit). The in vitro transcribed RNA (cRNA) was concentrated to 4 mg/ml.

EXAMPLE 2

Sequencing of the Rat vas deferens $P_{2X}$ Receptor cDNA

The cDNA insert was sequenced the exonuclease method (Henikoff *Meth. Enzymol.* 155 156–164 (1987)). The sequence is shown in FIG. 1.

EXAMPLE 3

Functional characterisation of the Rat vas deferens $P_{2X}$ Receptor cDNA in Oocytes 50 nl (200 ng) of RNA was injected into defolliculated *Xenopus oocytes*. After incubation for 2–6 days at 18° C., the oocytes were assayed for ATP-evoked currents by a two-electrode voltage clamp (GENECLAMP™) ; one electrode is to hold the voltage constant (at −100 mV), and the other is to measure the currents. A cDNA pool which showed ATP induced currents was subdivided to obtain a single clone ($P_{2X}$) Electrophysiological measurements were done at −100 mV, in a perfusion medium containing 96 mM NaCl, 2 mM KCl, 1.8 mM $CaCl_2$, 1 mM $MgCl_2$, 5 mM Hepes pH 7.6, and 5 mM sodium pyruvate. For dose-response curves and suramin inhibition, oocytes were injected with 100 ng $P_{2X}$ cRNA, and all recordings were performed at −60 mV, with $Ba^{2+}$ substituted for external $Ca^{2+}$ to prevent activation of endogenous $Ca^{2+}$-activated $Cl^-$ currents. Microelectrodes (0.5–2 MΩ) were filled with 3M KCl.

EXAMPLE 4

Functional characterisation of the Rat vas deferens $P_{2X}$ Receptor cDNA in HEX 293 Cells HEK 293 cells were transfected by the lipofectin method (Felgner et al., *Proc. Nat'l. Acad. Sci. USA* 84 7413–7417 (1987)) with $P_{2X}$-plasmid. DNA concentration used was 1 mg/2 ml medium placed into a 35 mm petri dish containing four 11 mm diameter coverslips on which HEK cells were placed at 10,000 cells per coverslip. Cells were exposed to lipofectin/DNA for 6 h and recordings made 16–36 h later; 40–60% of cells from which recordings were made exhibited $P_{2X}$ responses. Currents were recorded from HEK 293 cells using whole-cell recording methods and the AXOPATCH™ 200 amplifier (Axon Instruments); patch pipettes (5 MΩ) contained (mM) Cs or K aspartate 140, NaCl 5, EGTA 11, HEPES 5. The external solution was (mM) NaCl 150, KCl2, $CaCl_2$ 2, $MgCl_2$ 1, HEPES 5 and glucose 11; the pH and osmolarity of both solutions were maintained at 7.3 and 305 mosmol/l respectively. All recordings performed at room temperature. Data acquisition and analysis were performed using pCLAMP™ and AXOGRAPH™ software (Axon Instruments). Solutions for experiments examining calcium permeability of ATP currents in HEK cells contained (mM) : internal solution NaCl 150, HEPES 5, $CaCl_2$ 0.5 and EGTA 5 (free calcium concentration about 5 nM); external sodium solution NaCl 150, glucose 11, histidine 5, $CaCl_2$ 2; external calcium solution $CaCl_2$ 115, glucose 11 and histidine 5. The pH and osmolarity of the solutions were 7.4 and 295 mosmol/l respectively. For single channel measurements, a GENECLAMP™ 500 amplifier and outside-out recording methods were used (Adelman et al., *Neuron* 9 209–216 (1992)). Wax-coated patch pipettes (5–10 MΩ) contained (mM) K-gluconate 115, HEPES 5, BAPTA 5 and $MgCl_2$ 0.5, external solution was 96 mM NaCl, 2 mM KCl, 1.8 mM $CaCl_2$, 1 mM $MgCl_2$, 5 mM Hepes pH 7.6, and 5 mM sodium pyruvate. ATP was applied by U-tube typically for 1 s; data was sampled at 5 kHz in 2 s segments beginning 300 ms prior to onset of agonist (ATP) application and filtered at 1 kHz.

EXAMPLE 5

Transfection of the Rat vas deferens $P_{2X}$ Receptor cDNA into CHO and HEK293 Cells CHO cells were stably transfected by a method used for other ion channels (Claudio, *Meth. Enzymol.* 207 391–408 (1992)). Transfection was confirmed by a) electrophysiological recording and b) radioligand binding. ATP and other agonists (up to 30 μM) caused rapidly desensitising inward currents in 14 of 14 CHO cells stably transfected, and had no effect in 45 of 45 non-transfected cells. [³H] αβmethyleneATP binding was more than 600 cpm per million transfected cells with less than 80 cpm nonspecific binding.

Stable transfection of HEK293 cells was also achieved. This was confirmed by electrophysiological recording.

(ii) HUMAN $P_{2X}$ RECEPTOR

The materials and methods used in the human $P_{2X}$ receptor examples are set out below:

In Vitro translation

In vitro coupled transcription/translation were performed using Promega's TNT Coupled reticulocyte lysate Systems with or without 2 μl of canine pancreatic microsomal membranes (Promega). μg Circular pBKCMV-h$P_{2X}$ (0.5 ug) was transcribed with the T3 RNA polymerase as described in the system manual in a 25 μl reaction for 2 h are 30° C. Synthesized proteins (5 μl) were analysed by SDS-PAGE and autoradiography.

Differentiation of HL60 cells

HL60 cells (human promyelocytes ATCC CCL240) were passaged twice weekly in RPMI-1640 supplemented with 25 mnM HEPES, 2 mM Glutamax II, and 10% heat-inactivated fetal calf serum (GIBCO BRL) . For each experiment 33×10⁶ cells were resuspended at 2.5×10⁵ cells/ml in medium containing either phorbol mystate acetate (100 nM), 1. 1% DMSO, or dibutyryl cAMP (200 uM) (SIGMA) for the indicated times.

Northern blot analysis

PolyA⁺ RNAs were obtained from Clontech Laboratories Inc. (Palo Alto) except for the urinary bladder and HL60 mRNA which were prepared as described (Valera et al (1994)—supra) . Samples were quantified by measuring the O.D. at 260 nm, and by staining the membrane with methylene blue. The RNA were fractionated on a 1% agarose—6% formaldehyde gel and electroblotted to a non-charged nylon membrane (BDH). Prehybridisation at 68° C. was performed for 6 hours in hybridisation buffer (50% formamide, 5× SSC, 2% blocking buffer (Boehringer Mannheim), 0.1%6 laurolylsarcosine, 0.02% SDS). Hybridisation was overnight at 68° C. in fresh hybridisation buffer with a digoxigenin-UTP labelled riboprobe (100 ng/ml) corresponding to the entire h$P_2$x sequence. The membrane was washed at 68° C.; twice in 2× SSC+0.1% SDS, and twice in 0.1× SSC+0.1% SDS. Chemiluminescent detection of hybridisation was carried at room temperature as follows: the membrane was rinsed 5 min in buffer B1 (0.1 M maleic acid, 0.15 M NaCl, pH 7.5), saturated for 1 hour in 1% blocking buffer (B2), incubated 30 min with anti-digoxigenin-antibody alkaline phosphatase conjugated (750 u/ml, Boehringer Mannheim) diluted 1:15000 in B2, washed in B1+0.30% tween 20 (1× 5 min, 1× 15 min, 1× 1 h), equilibrated for 5 min in buffer B3 (0.1 M Tris HCl pH 9.5, 0.1 M NaCl, 50 mM $MgCl_2$), incubated 45–60 sec in lumigen PPD (Boehringer Mannheim) diluted 1:100 in B3. The humid membrane was sealed in a plastic bag, incubated 15 min at 37° C., and exposed 15 to 20 min to Hyperfilm-ECL (Amersham).

$P_{2X}$ expression into oocytes

Human urinary bladder $P_{2X}$ cDNA, subcloned into the pBKCMV expression vector, was linearized with NotI, and transcribed in vitro with T3 polymerase in the presence of cap analogue m7G(5')ppp(5')G. Defolliculated *Xenopus oocytes* (Bertrand et al, Electrophysiology of neuronal nicotinic acetylcholine receptors expressed in Xenopus oocytes following nuclear injection of genes or cDNAs Meth Neurosci 4: 174–193 (1991)) were injected with 50 ng of human $P_{2X}$ in vitro transcribed RNA, and incubated at 18° C. for 2–6 days in the ND96 solution (mM): NaCl 96, KCl 2, $MgCl_2$ 1, $CaCl_2$ 2, sodium pyruvate 5, HEPES 5, ph 7.6–7.5, penicillin (10 U/ml), and streptomycin (10 μg/ml).

Electrophysiology

Oocytes were placed in a 1 ml chamber and superfused at 2–3 ml/min with ND96 solution with 0.1 mM $BaCl_2$ replacing the 2 mM $CaCl_2$ to prevent activation of endogenous calcium-activated chloride currents (Barish, A transient calcium-dependent chloride current in the immature *Xenopus oocytes J Physiol* 342: 309–325 (1983)). Currents were measured using a two-electrode voltage-clamp amplifier (Geneclamp Axon Instruments) at a holding potential of –60 mV. Microelectrodes were filled with 3 M KCl (0.5–2 MΩ). Data were collected using PClamp software (Axon Instruments). ATP and other purinoceptor agonists were applied by a U-tube perfusion system (Fenwick et al, A patch clamp study of bovine chromaffin cells and their sensitivity to acetylcholine *J Physiol* 331: 577–597 (1982)) placed close (200–500 μm) to the oocyte. Initial studies showed that reproducible responses (<10% variation in peak amplitude) could be obtained when ATP (at concentrations up to 1 mM) was applied to $hP_{2X}$ injected oocytes for 5 s every 10 mins. Concentration response relationships to ATP and its analogs were determined by measuring the peak amplitude of responses to a 5 s application of agonist applied at 10 min intervals. Responses to agonists were normalized in each oocyte to the peak response evoked by 100 μM ATP; 100 μM ATP was usually applied at the beginning and at the end of an experiment to determine if there was any rundown of the response. No inward current was recorded in uninjected oocytes in response to application of purinoceptor agonists at the maximal concentration used (n=3 for each agonist). Antagonists were applied both in the superfusate and together with ATP in the U-tube solution. Antagonists were superfused for 5–10 min prior to the application of ATP.

Data analysis

Concentration response curves for purinoceptor agonists were fitted with a Hill slope of 1. Equi-effective concentrations i.e. concentration of agonist, giving 50% of the response to 100 μM ATP, ($EEC_{50}$) were determined from individual concentration response curves. For antagonists the concentration required to give 50% inhibition (IC50) of the response to 10 μM ATP (approximately 90% of peak response to ATP) were determined. Data are presented throughout as mean ± SEM for a given number of oocytes.

Drugs

Adenosine, adenosine 5'-monophosphate sodium salt (AMP), adenosine 5'-diphosphate sodium salt (ADP), adenosine 5'-triphosphate magnesium salt (ATP), adenosine 5'-O-(-3-thiophosphate) tetralithium salt (ATP-γ-S), uridine 5'-triphosphate sodium salt (UTP), α,β-methylene ATP lithium salt (α,β,-meATP), β,γ-methylene-D-ATP sodium salt (D-β,γ-meATP), 2'-3'-O-(4-benzoylbenzol)ATP tetraethylamonium salt (BzATP), 4,4'-diisothiocyanatostilbene 2,2'-disulphonic acid, disodium salt (DIDS) were obtained from Sigma. 2-MethylthioATP tetra sodium salt (2MeSATP), 2-chloro-ATP tetra sodium salt, and β-γ-methylene-1-ATP (1-β-γ-meATP) were obtained from RBl. Pyridoxal 5-phosphate monohydrate (Aldrich), p1, p5-di [adenosine-5'] pentaphosphate trilithium salt (AP5A) (Boehringer Mannheim), pyridoxal phosphate 6-azophenyl 2',4'-disulphonic acid (PPADS, gift of G. Lambrecht, University of Frankfurt) and suramin (Bayer) were tested. Drugs were prepared from frozen aliquots of stock solutions and diluted to give the required final concentration.

EXAMPLE 6

Sequence and characteristics of $hP_{2X}$ from urinary bladder

Isolation of human $P_{2X}$ cDNA

Human urinary bladder tissue was obtained from a cystectomy for a bladder tumor. The patient showed no symptoms of bladder instability or urodynamic abnormalities. Only those portions, surrounding the tumor, which appeared macroscopically normal (Palea et al—supra) were used. Total RNA was isolated by guanidinium isothiocyanate and poly $A^+$ RNA was purified as described (Valera et al (1994)—supra). Preparation of a cDNA library in λgt10, random primer labelling of a rat smooth muscle $P_{2X}$ probe (Valera et al (1994)—supra), low stringency hybridisation screening and lambda phage DNA isolation were all done by standard protocols (Sambrook et al, Molecular Cloning, A Laboratory Manual, 2nd edn., Cold Spring Harbor Laboratory Press, New York (1989)). Several independent phage isolates were examined and the cDNA insert from one was chosen for subcloning into Eco RI-Not I digested pBKCMV. This 2677 bp $hP_{2X}$ cDNA was sequenced as described (Valera et al (1994)—supra).

The 2677 bp cDNA, $hP_{2X}$, contained a single long open reading frame which corresponds to a protein of 399 amino acids (FIG. 4). This amino acid sequence is highly homologous with that of the $P_{2X}$ receptor, isolated from rat vas deferens (89% identity). There are two regions of hydrophobicity near either end of the protein which are sufficiently long to traverse the membrane but there is no hydrophobic N-terminal leader sequence. All five potential sites for glycosylation and all ten cysteine residues in the central section of the protein are conserved. In vitro translation of $hP_{2X}$ RNA in the presence of microsomes produced a 60 kD product, whereas translation in the absence of microsomes produced the 45 kD peptide (FIG. 6). 45 kD is the computed molecular weight, suggesting that the additional 15 kD results from glycosylation.

Some human urinary bladder $P_{2X}$ cDNA was used to transfect HEK293 cells. Stable transfection was confirmed by electrophysiological recording.

EXAMPLE 7

Distribution of human urinary bladder $P_{2X}$ mRNA

The distribution of the human urinary bladder $P_{2X}$ mRNA was examined by northern analysis. A single 2.6 kb mRNA species was observed in bladder, placenta, liver and adrenal gland (FIG. 8). In thymus, spleen, and lung samples, the 2.6 kb band plus additional higher molecular weight RNAs of 3.6 and 4.2 kb were seen. A smaller additional RNA species of 1.8 kb was observed in spleen and lung. No hybridisation was detected with brain mRNA.

EXAMPLE 8

Induction of $hP_{2X}$ mRNA in HL60 cells

A portion of the 3'-untranslated region had been previously deposited in the database (HSGS01701) as an expressed sequence tag for the differentiation of the human promyelocytic cell line, HL60 (Okubo unpublished). We examined the induction of $hP_{2X}$ mRNA in HL60 cells by Northern blot analysis (FIG. 7). HL60 cells can be differentiated into distinct lineages, depending on the inductant (Koeffler, Induction of Differentiation of Human Acute Myelogenous Leukemia Cells: Therapeutic Implications *Blood* 62: 709–721 (1983)). Induction of macrophage-like characteristics with phorbol diesters or granulocytic differentiation with DMSO or dibutryl cAMP, each produced an increase in $P_{2X}$ mRNA (FIG. 7, lane 6), HL60 RNA (lane 1–5) showed hybridisation of two bands (1.8 and 2.6 kb) and both of these were inducible. This contrasts with the bladder, where Northern analysis showed only a single RNA species (2.6 kb) (FIG. 7, lane 6).

EXAMPLE 9

Pharmacological characterization of $hP_{2X}$

Application of ATP (30 nM–1 mM) to oocytes injected with $hP_{2X}$ receptor RNA evoked inward currents (FIGS. 9, 10 and 11). Responses to low concentrations of ATP (30–300 nM) developed over 3–5 s. Higher concentrations of ATP (1 $\mu$M) evoked responses which peaked within 1–1.5 s and then declined during the continued application of ATP (40–60Cr of the peak amplitude after 5 s). The current returned to control values on washout of ATP. The peak amplitude of the inward current evoked by ATP was concentration-dependent (FIGS. 9, 10 and 11) and could be fitted by a curve with a Hill slope of 1 with a $EC_{50}$ of 0.82 $\mu$M. When ATP (100 $\mu$M) was applied for 5 s every 10 min, reproducible inward currents were recorded. This is in contrast to the responses of the $P_{2X}$ receptor clone from rat vas deferens where a second application of ATP (>1 $\mu$M) applied 10 mins after the first, evoked an inward current that was ~50% of the initial peak amplitude.

Concentration-response curves were constructed for a number of other $P_2$ purinoceptor agonists (FIGS. 9, 10 and 11). 2meSATP, 2-chloro-ATP, $\alpha,\beta$,-meATP and ADP were full agonists. BZATP, $AP_5A$ and ATP-$\gamma$-S produced maximal responses of about 65% of the maximal ATP response. The maximal responses to d and 1-$\beta$,$\gamma$-meATP were not determined. Adenosine, AMP and UTP (100 $\mu$M) evoked small inward currents (2.3±1.5, 6.08±2, and 3.7±1.8% of the response to 100 $\mu$M ATP respectively). The $EECD_{50}$ values and relative potencies of purinoceptor analogs are summarised in Table 1 below.

TABLE 1

| agonist | EEC50 ($\mu$M) | relative potency |
|---|---|---|
| ATP | 0.82 | 1 |
| 2MeSATP | 0.6 ± 0.1 | 1.36 |
| 2chloroATP | 0.76 ± 0.1 | 1.08 |
| AP5A | 2 ± 0.2 | 0.41 |
| $\alpha,\beta$-meATP | 3.6 ± 1.6 | 0.23 |
| BzATP | 4.2 ± 2.2 | 0.20 |
| ATP-$\gamma$-S | 10.6 ± 3.8 | 0.077 |
| d,$\beta$,$\gamma$-meATP | 24.1 ± 1.6 | 0.034 |
| ADP | 34.3 ± 16 | 0.024 |

EEC50: Equi-effective concentrations producing an inward current equivalent to 50% of the peak response to 100 $\mu$M ATP. EEC50 taken from individual fitted concentration response curves with a Hill slope of 1. EEC50 for ATP from mean data from all experiments. (n = 3–4).

EXAMPLE 10

Antagonist studies

The $P_2$-purinoceptor antagonist suramin (1–100 $\mu$M) shifted the concentration-response curve for ATP to the right. At 1 $\mu$M suramin the shift was almost parallel. The dissociation equilibrium constant ($K_B$) estimated from $K_B=1/(DR-1)$ where DR is the dose ratio was 130 nM. With higher concentrations of suramin the inhibition did not appear to be competitive. Under the present experimental conditions this $K_B$ estimate is higher than those reported previously for suramin (pA2 5.9, Trezise et al, *Br J Pharmacol* 112: 282–288 (1994)) $pK_B$ 5.2, von Kugelgen et al, Interaction of adenine nucleotides, UTP and suramin in mouse vas deferens: suramin-sensitive and suramin-insensitive components in the contractile effect of ATP *Naunyn Schmiedeberg's Arch Pharmacol* 342: 198–205 (1990)). The antagonism by suramin was fully reversed after 10 mins wash and indicates that the non-competitive antagonism at high concentrations is not due to irreversible binding of the antagonist to the receptor.

The putative $P_{2X}$ purinoceptor antagonists PPADS, DIDS and pyridoxal 5 phosphate (Ziganshin et al, Selective antagonism by PPADS at $P_{2X}$ purinoceptors in rabbit isolated blood vessels *Br J Pharmacol* 111: 923–929 (1994), Bultmann & Starke, Blockade by 4,4'-diisothiocyanatostilben-2,2'-disulphonate (DIDS) of $P_{2X}$ purinoceptors in rat vas deferens *Br J Pharmacol* 112: 690–694 (1994), Trezise et al, *Eur J Pharmacol* 259: 295–300 (1994)) inhibited inward currents evoked by 10 $\mu$M ATP (approximately $EC_{90}$ concentration) in a concentration dependent manner (FIGS. 12 and 13). Suramin PPADS and DIDS were equally effective in inhibiting ATP evoked currents ($IC_{50}$~1 $\mu$M). The IC 50 for $P_5P$ was~20 $\mu$M. PPADS and $P_5P$ antagonism was readily reversible on washout. In contrast, inhibitory effects of DIDS (100 $\mu$M) were very slow to reverse on washout.

(iii) RAT SUPERIOR CERVICAL GANGLION $P_{2X}$ RECEPTOR

EXAMPLE 11

Isolation and functional expression of a cDNA encoding a $P_{2X}$ receptor from rat superior cervical ganglion (referred to herein as clone 3)

A 440 bp fragment was amplified by polymerase chain-reaction (PCR) from rat testis cDNA, using degenerate primers based on conserved nucleotide sequences within the rat vas deferens $P_{2X}$ receptor cDNA and on the sequence of PC12 cDNA (Ehrlich H A (ed) *PCR Technology* MacMillan, Basingstoke (1989)). The primers used are given below:

Sense (SEQ ID NO 2)

5'  T G T/C G A A/G A/G T I T T/C I G G/C I T G G T G
    T/C C C 3'

Antisense (SEQ ID NO 3)

5'  G C A/G A A T/C C T A/G A A A/G T T A/G T/A A
    I C C 3'

(wherein I=Inosine and "T/C" indicates that either T or C is present at the position indicated (this applies mutatis mutandis to the other alternatives given).

The cloned PCR fragment was labelled and used as a hybridization probe for screening a rat testis cDNA bank in λZAP. One recombinant phage was positive, and its insert was excised and transferred to a plasmid (#432). This cDNA was 1500 bp with a single EcoR1 site (at position 1000, still in the open reading frame). The 5' end of the cDNA was too short to encode the entire N terminus.

Internal primers specific to the new sequence were made and the tissue distribution was tested by PCR. The candidate was present in mRNA prepared from phaeochromocytoma (PC12) cells, intestine and superior cervical ganglion (scg). The hybridization probe was therefore used to screen a rat scg cDNA bank in λgt10. From 30 initial positives, 20 pure phage DNA stocks were prepared; 19 were various portions of the candidate sequence, and the insert from one was transferred to plasmid (p457) and sequenced. The insert appeared to be a full length cDNA; it has a single open reading frame of 388 amino acids (FIG. 2). The insert from p457 was subcloned into pcDNA3 (p464) and used to transfect human embryonic kidney (HEK293) cells.

The functional characterisation of the clone illustrated in FIG. 2 (referred to herein as clone 3) was carried out by electrical recordings from transfected HEK293 cells and from oocytes injected with the in vitro transcribed RNA, as described in Example 4 for the rat vas deferens $P_{2X}$ receptor. Table A summarizes the main properties of clone 3 as compared to those of rat vas/human bladder cDNA clone, and the PC12 cDNA clone (provided by David Julius and Tony Brake of the University of California at San Francisco).

TABLE A

Functional Properties of 3 cloned $P_{2X}$ Receptors

|  | bladder | clone 3 | PC12 |
|---|---|---|---|
| kinetics |  |  |  |
| desensitization | very strong | very little | very little |
| rundown | profound | very little | very little |
| ionic permeability |  |  |  |
| monovalent | no differences | no differences | no differences |
| divalent (Ca$^{++}$) | high permeability | high permeability | high permeability |
| Ca$^{++}$ block | none | intermediate | very strong |
| agonist profile |  |  |  |
| ATP | 0.7 μM | 11 μM | 8 μM |
| α,β-meATP | 3 μM | >>100 mM | >>100 μM |
| antagonist profile |  |  |  |
| suramin | 1 μM | <40% block | 6 μM |
| PPADS | 1 μM | <30% block | 1 μM |

TABLE A-continued

Functional Properties of 3 cloned $P_{2X}$ Receptors

|  | bladder | clone 3 | PC12 |
|---|---|---|---|
| P-5-P | 6 μM | <40% block | 6 μM |
| DIDS | 1 μM |  | >100 μM |

The main functional properties of clone 3 are as follows. (a) The currents evoked by ATP show little or no decline during applications of several seconds; that is, there is little desensitisation (FIG. 14). (b) The relative permeabilities of the ionic pore to sodium, potassium, cesium, tetraethylammonium and to calcium are not different to those observed for the rat vas deferens/human bladder or the PC12 forms of the receptor. (c) Extracellular calcium (30 mM) inhibits the inward current through the $P_{2X}$ receptor channel of the PC12 form whereas it does not block current through the rat vas deferens/human bladder form; clone 3 is intermediate in sensitivity. (d) The effectiveness of agonists that are structurally related to ATP is the same as that found for the PC12 form; most notably, αβmethylene ATP has little or no agonist action (FIG. 14). (e) Currents activated by ATP at the clone 3 receptor were much less sensitive to antagonism by suramin., pyridoxal 5'-phosphate and pyridoxal-6-azophenyl-2',4'-disulphonic acid (PPADS) than were similar current mediated by the other two forms (rat vas deferens/human bladder; PC12) (FIG. 15).

(iv) RAT DORSAL ROOT GANGLION $P_{2X}$ RECEPTOR

EXAMPLE 12

Isolation of a cDNA encoding a $P_{2X}$ receptor from a rat dorsal root ganglion By using PCR with the same primers as used in Example 11 above, but using different cDNA sources, further $P_{2X}$ family members can be found.

Using this method, rat dorsal root ganglion $P_{2X}$ receptor cDNA was isolated. FIG. 1B shows the cDNA sequence of this clone (referred to herein as clone 6), together with the putative amino acid sequence. The portions underlined in this figure correspond to the PCR primers initially used.

A similar procedure to that described in Example 11 was then used to isolate the full length cDNA.

We claim:

1. A recombinant or isolated DNA molecule encoding a $P_{2X}$ receptor wherein the receptor has the amino sequence shown in SEQ ID NO:5, SEQ ID NO:7, SEQ ID NO:9 or SEQ ID NO:11.

2. A recombinant or isolated DNA molecule encoding a $P_{2X}$ receptor wherein the receptor has the amino sequence shown in SEQ ID NO:5 or SEQ ID NO:11.

3. A recombinant or isolated DNA molecule encoding a $P_{2X}$ receptor wherein the receptor has the amino sequence shown in SEQ ID NO:5.

4. The DNA molecule as claimed in any one of claims 1 to 3, which encodes a receptor having human $P_{2X}$ receptor activity as a ligand gated ion channel susceptible to blockade with suramin.

5. The DNA molecule as claimed in any one of claims 1 to 3, which is cDNA.

6. A vector comprising a DNA molecule as claimed in claim 1.

7. A host cell transformed or transfected with the vector as claimed in claim 6.

8. A host cell as claimed in claim 7 which is a stably transfected mammalian cell which expresses a $P_{2X}$ receptor active as a ligand gated ion channel susceptible to blockade with suramin.

9. A method for obtaining a $P_{2X}$ receptor active as a ligand gated ion channel susceptible to blockade with suramin comprising culturing the host cell according to claim 8 under conditions which result in the expression of said $P_{2X}$ receptor and purifying the expressed $P_{2X}$ receptor.

10. A preparation of $P_{2X}$ receptor which is free of protein with which it is naturally associated wherein the receptor has the amino acid sequence shown in SEQ ID NO:5, SEQ ID NO:7, SEQ ID NO:9 or SEQ ID NO:11.

11. A recombinant or isolated DNA molecule encoding a $P_{2X}$ receptor which has the nucleotide sequence shown in SEQ ID NO:4, SEQ ID NO:6, SEQ ID NO:8 or SEQ ID NO:10.

12. A recombinant or isolated DNA molecule encoding a $P_{2X}$ receptor which has the nucleotide coding sequence of SEQ ID NO:4 (nucleotides 210–1406), SEQ ID NO:6 (nucleotides 101–1264), SEQ ID NO:8 (nucleotides 163–1353) or SEQ ID NO:10 (nucleotides 174–1370).

* * * * *

SEQUENCE LISTING (1) GENERAL INFORMATION:

(iii) NUMBER OF SEQUENCES: 11

(2) INFORMATION FOR SEQ ID NO: 1:

(i) SEQUENCE CHARACTERISTICS:
      (A) LENGTH: 33 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO: 1:

```
GAGAGAGAGA GCGGCCGCTT TTTTTTTTTT TTT                              33
```

(2) INFORMATION FOR SEQ ID NO: 2:

(i) SEQUENCE CHARACTERISTICS:
      (A) LENGTH: 23 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO: 2:

```
TGNGANNTNT NNGNNTGGTG NCC                                         23
```

(2) INFORMATION FOR SEQ ID NO: 3:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO: 3:

```
GCNAANCTNA ANTTNNANCC                                             20
```

(2) INFORMATION FOR SEQ ID NO: 4:

(i) SEQUENCE CHARACTERISTICS:
      (A) LENGTH: 1837 base pairs
      (B) TYPE: nucleic acid
      (C) STRANDEDNESS: single
      (D) TOPOLOGY: linear (ii) MOLECULE TYPE: cDNA (vii) IMMEDIATE SOURCE:
      (B) CLONE: rat P2x from vas deferens (xi) SEQUENCE DESCRIPTION: SEQ ID NO: 4:

```
GCCAAAAGCT GTTCTGATCA CCCAGGGTTT TTCCTCCCAA CCCAGACCCC ACCATCGAAC   60

CTCCAACTCT GGTCCCACCT AGCCTGCTCT GTCCTTAAGG GGCCGGGAAG CCCCAGTCAC  120

TCCACTGCTA TTGTAGATGC AGATGGTGGC CTGCCCTTGA CCATAGAGGC CGTGTGGGGT  180

GTTCATCTCT GAGCCCCTTC TGGCCCACC ATG GCT CGG CGG CTG CAA GAT GAG   233
                                 Met Ala Arg Arg Leu Gln Asp Glu
                                  1               5

CTG TCA GCC TTC TTC TTT GAA TAT GAC ACT CCC CGG ATG GTG CTG GTA  281
Leu Ser Ala Phe Phe Phe Glu Tyr Asp Thr Pro Arg Met Val Leu Val
```

-continued

```
              10                  15                  20
CGA AAC AAG AAG GTG GGA GTC ATT TTC CGT CTG ATC CAG TTG GTG GTT    329
Arg Asn Lys Lys Val Gly Val Ile Phe Arg Leu Ile Gln Leu Val Val
 25                  30                  35                  40

CTG GTC TAC GTC ATT GGG TGG GTG TTT GTC TAT GAA AAA GGA TAC CAG    377
Leu Val Tyr Val Ile Gly Trp Val Phe Val Tyr Glu Lys Gly Tyr Gln
                     45                  50                  55

ACC TCA AGT GAC CTC ATC AGC AGT GTG TCC GTG AAG CTC AAG GGC TTG    425
Thr Ser Ser Asp Leu Ile Ser Ser Val Ser Val Lys Leu Lys Gly Leu
                 60                  65                  70

GCT GTG ACC CAG CTC CAG GGC CTG GGA CCC CAG GTC TGG GAC GTG GCT    473
Ala Val Thr Gln Leu Gln Gly Leu Gly Pro Gln Val Trp Asp Val Ala
             75                  80                  85

GAC TAT GTC TTC CCA GCA CAC GGG GAC AGC TCC TTT GTA GTT ATG ACC    521
Asp Tyr Val Phe Pro Ala His Gly Asp Ser Ser Phe Val Val Met Thr
         90                  95                 100

AAC TTC ATC GTG ACC CCT CAG CAG ACT CAA GGC CAT TGT GCA GAG AAC    569
Asn Phe Ile Val Thr Pro Gln Gln Thr Gln Gly His Cys Ala Glu Asn
105                 110                 115                 120

CCA GAA GGT GGC ATA TGC CAG GAT GAC AGT GGC TGC ACT CCA GGA AAA    617
Pro Glu Gly Gly Ile Cys Gln Asp Asp Ser Gly Cys Thr Pro Gly Lys
                125                 130                 135

GCA GAA AGG AAA GCC CAA GGT ATT CGC ACA GGC AAC TGT GTG CCC TTC    665
Ala Glu Arg Lys Ala Gln Gly Ile Arg Thr Gly Asn Cys Val Pro Phe
            140                 145                 150

AAT GGC ACT GTG AAG ACA TGT GAG ATC TTT GGT TGG TGT CCT GTA GAG    713
Asn Gly Thr Val Lys Thr Cys Glu Ile Phe Gly Trp Cys Pro Val Glu
        155                 160                 165

GTG GAT GAC AAG ATC CCA AGC CCT GCT CTT CTT CGT GAG GCT GAG AAC    761
Val Asp Asp Lys Ile Pro Ser Pro Ala Leu Leu Arg Glu Ala Glu Asn
    170                 175                 180

TTC ACC CTC TTC ATC AAA AAC AGC ATC AGC TTT CCA CGC TTC AAG GTC    809
Phe Thr Leu Phe Ile Lys Asn Ser Ile Ser Phe Pro Arg Phe Lys Val
185                 190                 195                 200

AAC AGG CGC AAC CTG GTA GAG GAG GTG AAC GGC ACC TAC ATG AAG AAG    857
Asn Arg Arg Asn Leu Val Glu Glu Val Asn Gly Thr Tyr Met Lys Lys
                205                 210                 215

TGC CTC TAT CAC AAG ATT CAA CAC CCC CTG TGC CCA GTC TTC AAC CTT    905
Cys Leu Tyr His Lys Ile Gln His Pro Leu Cys Pro Val Phe Asn Leu
            220                 225                 230

GGC TAT GTG GTG CGA GAG TCA GGC CAG GAC TTC CGC AGC CTT GCT GAG    953
Gly Tyr Val Val Arg Glu Ser Gly Gln Asp Phe Arg Ser Leu Ala Glu
        235                 240                 245

AAG GGT GGG GTG GTT GGT ATC ACC ATT GAC TGG AAG TGT GAT CTG GAC   1001
Lys Gly Gly Val Val Gly Ile Thr Ile Asp Trp Lys Cys Asp Leu Asp
    250                 255                 260

TGG CAC GTT CGG CAC TGC AAA CCC ATC TAC CAG TTC CAC GGA CTG TAT   1049
Trp His Val Arg His Cys Lys Pro Ile Tyr Gln Phe His Gly Leu Tyr
265                 270                 275                 280

GGG GAG AAG AAC CTG TCT CCA GGC TTC AAC TTC AGA TTT GCC AGG CAT   1097
Gly Glu Lys Asn Leu Ser Pro Gly Phe Asn Phe Arg Phe Ala Arg His
                285                 290                 295

TTC GTG CAG AAT GGG ACA AAC CGT CGT CAC CTC TTC AAG GTG TTT GGG   1145
Phe Val Gln Asn Gly Thr Asn Arg Arg His Leu Phe Lys Val Phe Gly
            300                 305                 310

ATT CAC TTT GAT ATC CTT GTG GAT GGC AAG GCT GGG AAG TTT GAC ATC   1193
Ile His Phe Asp Ile Leu Val Asp Gly Lys Ala Gly Lys Phe Asp Ile
        315                 320                 325

ATC CCT ACT ATG ACT ACT ATC GGT TCT GGG ATT GGC ATC TTT GGA GTG   1241
Ile Pro Thr Met Thr Thr Ile Gly Ser Gly Ile Gly Ile Phe Gly Val
```

```
                      330                 335                 340
GCC ACA GTG CTT TGT GAT CTC TTA TTG CTC CAC ATC CTG CCT AAG AGG         1289
Ala Thr Val Leu Cys Asp Leu Leu Leu Leu His Ile Leu Pro Lys Arg
345                 350                 355                 360

CAC TAC TAC AAG CAG AAG AAG TTC AAA TAT GCC GAG GAC ATG GGG CCG         1337
His Tyr Tyr Lys Gln Lys Lys Phe Lys Tyr Ala Glu Asp Met Gly Pro
                    365                 370                 375

GGA GAG GGT GAA CAT GAC CCC GTG GCC ACC AGC TCC ACT CTG GGC CTG         1385
Gly Glu Gly Glu His Asp Pro Val Ala Thr Ser Ser Thr Leu Gly Leu
                380                 385                 390

CAG GAG AAC ATG AGG ACC TCC TGACCTTAGT CTTGAGATCC GGACTTGACG            1436
Gln Glu Asn Met Arg Thr Ser
            395

CAGTGTGTGG CTTCCGGCAA GGGCTGATGG CTTTGAGCCA GGGCAGAGGG CATTCCCAGA       1496

GGCTTTCCTG CAAGGCAGAC ACCAGTGGCC CTCTGGTTCA GCATGAAGAC AGGCAAGACT       1556

TTGGATTTCA GAGCTCTGGT TTCAGTTCCA CATGTCCCTT CCTGAGGGAT GCCTCCTCCA       1616

GTTTTCACCA ATTTGGGTTC ATATGGCTGG GCCCCTCACA CATCTATACT CTAGCTTTGT       1676

GCTTAAGGCT CAGGCTGTCA TTGTCTTTCC CACAGCCTTA CCTGCCTAGA TTTGGGCTCT       1736

TCCACATGGT AGCCACTAGC CAGATGTGTC AGTTTGAACT TTAATTAAAA TATAATAAAA       1796

AAAAAAAAAA AAAAAAAAA AAAAAAAAAA AAAAAAAAA A                            1837

(2) INFORMATION FOR SEQ ID NO: 5:

(i) SEQUENCE CHARACTERISTICS:
        (A) LENGTH: 399 amino acids
        (B) TYPE: amino acid
        (D) TOPOLOGY: linear (ii) MOLECULE TYPE: protein (xi) SEQUENCE DESCRIPTION: SEQ ID NO: 5:

Met Ala Arg Arg Leu Gln Asp Glu Leu Ser Ala Phe Phe Phe Glu Tyr
 1               5                  10                  15

Asp Thr Pro Arg Met Val Leu Val Arg Asn Lys Lys Val Gly Val Ile
            20                  25                  30

Phe Arg Leu Ile Gln Leu Val Val Leu Val Tyr Val Ile Gly Trp Val
        35                  40                  45

Phe Val Tyr Glu Lys Gly Tyr Gln Thr Ser Ser Asp Leu Ile Ser Ser
    50                  55                  60

Val Ser Val Lys Leu Lys Gly Leu Ala Val Thr Gln Leu Gln Gly Leu
65                  70                  75                  80

Gly Pro Gln Val Trp Asp Val Ala Asp Tyr Val Phe Pro Ala His Gly
                85                  90                  95

Asp Ser Ser Phe Val Val Met Thr Asn Phe Ile Val Thr Pro Gln Gln
            100                 105                 110

Thr Gln Gly His Cys Ala Glu Asn Pro Glu Gly Gly Ile Cys Gln Asp
        115                 120                 125

Asp Ser Gly Cys Thr Pro Gly Lys Ala Glu Arg Lys Ala Gln Gly Ile
    130                 135                 140

Arg Thr Gly Asn Cys Val Pro Phe Asn Gly Thr Val Lys Thr Cys Glu
145                 150                 155                 160

Ile Phe Gly Trp Cys Pro Val Glu Val Asp Asp Lys Ile Pro Ser Pro
                165                 170                 175

Ala Leu Leu Arg Glu Ala Glu Asn Phe Thr Leu Phe Ile Lys Asn Ser
            180                 185                 190
```

```
Ile Ser Phe Pro Arg Phe Lys Val Asn Arg Arg Asn Leu Val Glu Glu
        195                 200                 205

Val Asn Gly Thr Tyr Met Lys Lys Cys Leu Tyr His Lys Ile Gln His
    210                 215                 220

Pro Leu Cys Pro Val Phe Asn Leu Gly Tyr Val Arg Glu Ser Gly
225                 230                 235                 240

Gln Asp Phe Arg Ser Leu Ala Glu Lys Gly Val Val Gly Ile Thr
                245                 250                 255

Ile Asp Trp Lys Cys Asp Leu Asp Trp His Val Arg His Cys Lys Pro
            260                 265                 270

Ile Tyr Gln Phe His Gly Leu Tyr Gly Glu Lys Asn Leu Ser Pro Gly
        275                 280                 285

Phe Asn Phe Arg Phe Ala Arg His Phe Val Gln Asn Gly Thr Asn Arg
    290                 295                 300

Arg His Leu Phe Lys Val Phe Gly Ile His Phe Asp Ile Leu Val Asp
305                 310                 315                 320

Gly Lys Ala Gly Lys Phe Asp Ile Ile Pro Thr Met Thr Thr Ile Gly
                325                 330                 335

Ser Gly Ile Gly Ile Phe Gly Val Ala Thr Val Leu Cys Asp Leu Leu
            340                 345                 350

Leu Leu His Ile Leu Pro Lys Arg His Tyr Tyr Lys Gln Lys Lys Phe
        355                 360                 365

Lys Tyr Ala Glu Asp Met Gly Pro Gly Glu Gly His Asp Pro Val
    370                 375                 380

Ala Thr Ser Ser Thr Leu Gly Leu Gln Glu Asn Met Arg Thr Ser
385                 390                 395

(2) INFORMATION FOR SEQ ID NO: 6:

(i) SEQUENCE CHARACTERISTICS:
        (A) LENGTH: 1997 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 6:

CGCAGCGAGC CTGCCGGAGC TGGTGGGTGG AGCTACGACC GGGAGCCGAC GGTGGCGAGG         60

GGACCCACAG TGTCCAAGGC GCGGAGCGGT CGGCGGAGCC ATG GCG GGC TGC TGC         115
                                              Met Ala Gly Cys Cys
                                              400

TCC GTG CTC GGG TCC TTC CTG TTC GAG TAC GAC ACG CCG CGC ATC GTG         163
Ser Val Leu Gly Ser Phe Leu Phe Glu Tyr Asp Thr Pro Arg Ile Val
405                 410                 415                 420

CTC ATC CGC AGC CGT AAA GTG GGG CTC ATG AAC CGC GCG GTG CAG CTG         211
Leu Ile Arg Ser Arg Lys Val Gly Leu Met Asn Arg Ala Val Gln Leu
                425                 430                 435

CTC ATC CTG GCT TAC GTC ATC GGG TGG GTG TTC GTG TGG GAA AAG GGC         259
Leu Ile Leu Ala Tyr Val Ile Gly Trp Val Phe Val Trp Glu Lys Gly
            440                 445                 450

TAC CAG GAA ACG GAC TCC GTG GTC AGC TCG GTG ACA ACC AAA GCC AAA         307
Tyr Gln Glu Thr Asp Ser Val Val Ser Ser Val Thr Thr Lys Ala Lys
        455                 460                 465

GGT GTG GCT GTG ACC AAC ACC TCT CAG CTT GGA TTC CGG ATC TGG GAC         355
Gly Val Ala Val Thr Asn Thr Ser Gln Leu Gly Phe Arg Ile Trp Asp
    470                 475                 480

GTG GCG GAC TAT GTG ATT CCA GCT CAG GAG GAA AAC TCC CTC TTC ATT         403
Val Ala Asp Tyr Val Ile Pro Ala Gln Glu Glu Asn Ser Leu Phe Ile
```

-continued

|     |     |     |     |     |     |     |     |     |     |     |     |     |     |     |     |     |
|---|---|---|---|---|---|---|---|---|---|---|---|---|---|---|---|---|
| 485 | | | | 490 | | | | 495 | | | | 500 | | | | |
| ATG | ACC | AAC | ATG | ATT | GTC | ACC | GTG | AAC | CAG | ACA | CAG | AGC | ACC | TGT | CCA | 451 |
| Met | Thr | Asn | Met | Ile | Val | Thr | Val | Asn | Gln | Thr | Gln | Ser | Thr | Cys | Pro | |
| | | | | | | 505 | | | | 510 | | | | 515 | | |

```
ATG ACC AAC ATG ATT GTC ACC GTG AAC CAG ACA CAG AGC ACC TGT CCA         451
Met Thr Asn Met Ile Val Thr Val Asn Gln Thr Gln Ser Thr Cys Pro
                505                 510                 515

GAG ATT CCT GAT AAG ACC AGC ATT TGT AAT TCA GAC GCC GAC TGC ACT         499
Glu Ile Pro Asp Lys Thr Ser Ile Cys Asn Ser Asp Ala Asp Cys Thr
            520                 525                 530

CCT GGC TCC GTG GAC ACC CAC AGC AGT GGA GTT GCG ACT GGA AGA TGT         547
Pro Gly Ser Val Asp Thr His Ser Ser Gly Val Ala Thr Gly Arg Cys
        535                 540                 545

GTT CCT TTC AAT GAG TCT GTG AAG ACC TGT GAG GTG GCT GCA TGG TGC         595
Val Pro Phe Asn Glu Ser Val Lys Thr Cys Glu Val Ala Ala Trp Cys
    550                 555                 560

CCG GTG GAG AAC GAC GTT GGC GTG CCA ACG CCG GCT TTC TTA AAG GCT         643
Pro Val Glu Asn Asp Val Gly Val Pro Thr Pro Ala Phe Leu Lys Ala
565                 570                 575                 580

GCA GAA AAC TTC ACC CTC TTG GTA AAG AAC AAC ATC TGG TAC CCC AAG         691
Ala Glu Asn Phe Thr Leu Leu Val Lys Asn Asn Ile Trp Tyr Pro Lys
                585                 590                 595

TTT AAC TTC AGC AAG AGG AAC ATC CTC CCC AAC ATC ACC ACG TCC TAC         739
Phe Asn Phe Ser Lys Arg Asn Ile Leu Pro Asn Ile Thr Thr Ser Tyr
            600                 605                 610

CTC AAA TCG TGC ATT TAC AAT GCT CAA ACG GAT CCC TTC TGC CCC ATA         787
Leu Lys Ser Cys Ile Tyr Asn Ala Gln Thr Asp Pro Phe Cys Pro Ile
        615                 620                 625

TTC CGT CTT GGC ACA ATC GTG GGG GAC GCG GGA CAT AGC TTC CAG GAG         835
Phe Arg Leu Gly Thr Ile Val Gly Asp Ala Gly His Ser Phe Gln Glu
    630                 635                 640

ATG GCA GTT GAG GGA GGC ATC ATG GGT ATC CAG ATC AAG TGG GAC TGC         883
Met Ala Val Glu Gly Gly Ile Met Gly Ile Gln Ile Lys Trp Asp Cys
645                 650                 655                 660

AAC CTG GAT AGA GCC GCC TCC CTT TGC CTG CCC AGA TAT TCC TTC CGG         931
Asn Leu Asp Arg Ala Ala Ser Leu Cys Leu Pro Arg Tyr Ser Phe Arg
                665                 670                 675

CGC CTG GAC ACC CGG GAC CTG GAA CAC AAT GTG TCT CCT GGC TAC AAT         979
Arg Leu Asp Thr Arg Asp Leu Glu His Asn Val Ser Pro Gly Tyr Asn
            680                 685                 690

TTC AGG TTT GCC AAG TAC TAC AGG GAC CTG GCC GGC AAA GAG CAG CGC        1027
Phe Arg Phe Ala Lys Tyr Tyr Arg Asp Leu Ala Gly Lys Glu Gln Arg
        695                 700                 705

ACA CTC ACC AAG GCG TAC GGC ATC CGC TTT GAC ATC ATC GTG TTT GGA        1075
Thr Leu Thr Lys Ala Tyr Gly Ile Arg Phe Asp Ile Ile Val Phe Gly
    710                 715                 720

AAG GCT GGG AAG TTT GAC ATC ATC CCT ACC ATG ATC AAC GTT GGC TCT        1123
Lys Ala Gly Lys Phe Asp Ile Ile Pro Thr Met Ile Asn Val Gly Ser
725                 730                 735                 740

GGC TTG GCG CTC CTC GGG GTG GCG ACG GTG CTC TGT GAC GTC ATA GTC        1171
Gly Leu Ala Leu Leu Gly Val Ala Thr Val Leu Cys Asp Val Ile Val
                745                 750                 755

CTC TAC TGC ATG AAG AAG AAA TAC TAC TAC CGG GAC AAG AAA TAT AAG        1219
Leu Tyr Cys Met Lys Lys Lys Tyr Tyr Tyr Arg Asp Lys Lys Tyr Lys
            760                 765                 770

TAT GTG GAA GAC TAC GAG CAG GGT CTT TCG GGG GAG ATG AAC CAG            1264
Tyr Val Glu Asp Tyr Glu Gln Gly Leu Ser Gly Glu Met Asn Gln
        775                 780                 785

TGACGCCTAA AGTTACATTT CCACCCCGCT CAGCCCGCGA AGCAGAAAGA TGGGGAGAGA     1324

TGGCTACTGC GTCTGTCACT CTAGAGAAAG CTCCAGAGTT TCAGCTCAGT TCTCCACTCC     1384

ACAAATACTC AGGGTTGCCA AGCACATCTT GTTGGAGCCC GGCTCTTGCT CTGCTGCTCA     1444
```

-continued

```
GATGGGCTTC CAGATACAAG AATCCTCCTG CTTCTGCCTC TAGGAATGCT GGGATCAAAC    1504

ATGTCACTTG CAATGCCCAT TTCCCATGGG GAGTTTGGCA TTTTTTACAT TTTACCCTTT    1564

CCTTTTGTAT ACATCTAAGG CTGCCCTCAG ACGCAAGACG TTCTTCCACC CTATACACCC    1624

TTTTAATCTC ACTGTGTGTG GGAGGGGGGT CGTTTGCACA CGACGCACGG TGGATGTCTG    1684

GTGTGCTGTT GGCTGGGCCA CCTGTGGCTT ATACAGTGTG AGCGTATGGA GGTAGGAAGG    1744

GTCTGAGAGC AGAGACACTG CTGTGGCTTA CGGACAGGCC CAGGCTCTGT CCACGCACTT    1804

TATTTCTAAG GAAGGAGGCT CTCTCAGGTG CTGTCAGCAG GCCTGGGACA CCATTCCTCT    1864

TCCCTATAAT CAGAGAAGTT GTCCTTGTAG CAAAGGCAGG GTTAGCTTTT CCTTTTATAA    1924

GGGCTGTGTT GAAATGACCT AGGACCAAAC ATTAAAAGAA ATAATTTTTT AAAAAAAAAA    1984

AAAAAAAAAA AAA                                                       1997
```

(2) INFORMATION FOR SEQ ID NO: 7:

(i) SEQUENCE CHARACTERISTICS:
        (A) LENGTH: 388 amino acids
        (B) TYPE: amino acid
        (D) TOPOLOGY: linear (ii) MOLECULE TYPE: protein (xi) SEQUENCE DESCRIPTION: SEQ ID NO: 7:

```
Met Ala Gly Cys Cys Ser Val Leu Gly Ser Phe Leu Phe Glu Tyr Asp
 1               5                  10                  15

Thr Pro Arg Ile Val Leu Ile Arg Ser Arg Lys Val Gly Leu Met Asn
            20                  25                  30

Arg Ala Val Gln Leu Leu Ile Leu Ala Tyr Val Ile Gly Trp Val Phe
        35                  40                  45

Val Trp Glu Lys Gly Tyr Gln Glu Thr Asp Ser Val Val Ser Ser Val
    50                  55                  60

Thr Thr Lys Ala Lys Gly Val Ala Val Thr Asn Thr Ser Gln Leu Gly
65                  70                  75                  80

Phe Arg Ile Trp Asp Val Ala Asp Tyr Val Ile Pro Ala Gln Glu Glu
                85                  90                  95

Asn Ser Leu Phe Ile Met Thr Asn Met Ile Val Thr Val Asn Gln Thr
            100                 105                 110

Gln Ser Thr Cys Pro Glu Ile Pro Asp Lys Thr Ser Ile Cys Asn Ser
        115                 120                 125

Asp Ala Asp Cys Thr Pro Gly Ser Val Asp Thr His Ser Ser Gly Val
    130                 135                 140

Ala Thr Gly Arg Cys Val Pro Phe Asn Glu Ser Val Lys Thr Cys Glu
145                 150                 155                 160

Val Ala Ala Trp Cys Pro Val Glu Asn Asp Val Gly Val Pro Thr Pro
                165                 170                 175

Ala Phe Leu Lys Ala Ala Glu Asn Phe Thr Leu Leu Val Lys Asn Asn
            180                 185                 190

Ile Trp Tyr Pro Lys Phe Asn Phe Ser Lys Arg Asn Ile Leu Pro Asn
        195                 200                 205

Ile Thr Thr Ser Tyr Leu Lys Ser Cys Ile Tyr Asn Ala Gln Thr Asp
    210                 215                 220

Pro Phe Cys Pro Ile Phe Arg Leu Gly Thr Ile Val Gly Asp Ala Gly
225                 230                 235                 240

His Ser Phe Gln Glu Met Ala Val Glu Gly Gly Ile Met Gly Ile Gln
                245                 250                 255
```

-continued

```
Ile Lys Trp Asp Cys Asn Leu Asp Arg Ala Ala Ser Leu Cys Leu Pro
        260                 265                 270

Arg Tyr Ser Phe Arg Arg Leu Asp Thr Arg Asp Leu Glu His Asn Val
        275                 280                 285

Ser Pro Gly Tyr Asn Phe Arg Phe Ala Lys Tyr Tyr Arg Asp Leu Ala
290                 295                 300

Gly Lys Glu Gln Arg Thr Leu Thr Lys Ala Tyr Gly Ile Arg Phe Asp
305                 310                 315                 320

Ile Ile Val Phe Gly Lys Ala Gly Lys Phe Asp Ile Ile Pro Thr Met
                325                 330                 335

Ile Asn Val Gly Ser Gly Leu Ala Leu Leu Gly Val Ala Thr Val Leu
                340                 345                 350

Cys Asp Val Ile Val Leu Tyr Cys Met Lys Lys Tyr Tyr Tyr Arg
                355                 360                 365

Asp Lys Lys Tyr Lys Tyr Val Glu Asp Tyr Glu Gln Gly Leu Ser Gly
370                 375                 380

Glu Met Asn Gln
385
```

(2) INFORMATION FOR SEQ ID NO: 8:

(i) SEQUENCE CHARACTERISTICS:
        (A) LENGTH: 1753 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 8:

```
CACTGGGCTA CAGTTGCCTG GCTTACAGGA ACTGGCTCTT TTCCTCAAGC CTCATTAAGC        60

AGCCCACTCC AGTTCTTGAT CTTTGTCTCC CAGTCCTGAA GTCCTTTCTC TCCTTAGGCT       120

GCATCCACAG CCCTTCTAAG TGGCTGTGAG CAGTTTCTCA GT ATG AAC TGT ATA          174
                                              Met Asn Cys Ile
                                                      390

TCA GAC TTC TTC ACC TAC GAG ACT ACC AAG TCG GTG GTT GTG AAG AGC         222
Ser Asp Phe Phe Thr Tyr Glu Thr Thr Lys Ser Val Val Val Lys Ser
        395                 400                 405

TGG ACC ATT GGG ATC ATC AAC CGA GCC GTC CAG CTG CTG ATT ATC TCC         270
Trp Thr Ile Gly Ile Ile Asn Arg Ala Val Gln Leu Leu Ile Ile Ser
        410                 415                 420

TAC TTT GTG GGG TGG GTT TTC TTG CAT GAG AAG GCC TAC CAA GTG AGG         318
Tyr Phe Val Gly Trp Val Phe Leu His Glu Lys Ala Tyr Gln Val Arg
425                 430                 435                 440

GAC ACC GCC ATT GAG TCC TCA GTA GTT ACA AAG GTG AAA GGC TTC GGG         366
Asp Thr Ala Ile Glu Ser Ser Val Val Thr Lys Val Lys Gly Phe Gly
                445                 450                 455

CGC TAT GCC AAC AGA GTC ATG GAC GTG TCG GAT TAT GTG ACC CCA CCC         414
Arg Tyr Ala Asn Arg Val Met Asp Val Ser Asp Tyr Val Thr Pro Pro
                460                 465                 470

CAG GGC ACC TCT GTC TTT GTC ATC ATC ACC AAA ATG ATC GTT ACT GAA         462
Gln Gly Thr Ser Val Phe Val Ile Ile Thr Lys Met Ile Val Thr Glu
        475                 480                 485

AAT CAA ATG CAA GGA TTC TGT CCA GAG AAT GAA GAG AAG TAC CGC TGT         510
Asn Gln Met Gln Gly Phe Cys Pro Glu Asn Glu Glu Lys Tyr Arg Cys
        490                 495                 500

GTG TCT GAC AGC CAG TGT GGG CCT GAA CGC TTC CCA GGT GGG GGG ATC         558
Val Ser Asp Ser Gln Cys Gly Pro Glu Arg Phe Pro Gly Gly Gly Ile
505                 510                 515                 520
```

```
CTC ACC GGC CGC TGC GTG AAC TAC AGC TCT GTT CTC CGG ACC TGT GAG        606
Leu Thr Gly Arg Cys Val Asn Tyr Ser Ser Val Leu Arg Thr Cys Glu
            525                 530                 535

ATC CAG GGC TGG TGC CCC ACT GAG GTG GAC ACC GTG GAG ATG CCT ATC        654
Ile Gln Gly Trp Cys Pro Thr Glu Val Asp Thr Val Glu Met Pro Ile
            540                 545                 550

ATG ATG GAG GCT GAG AAC TTC ACC ATT TTC ATC AAG AAC AGC ATC CGT        702
Met Met Glu Ala Glu Asn Phe Thr Ile Phe Ile Lys Asn Ser Ile Arg
            555                 560                 565

TTC CCT CTC TTC AAC TTT GAG AAG GGA AAC CTC CTG CCT AAC CTC ACC        750
Phe Pro Leu Phe Asn Phe Glu Lys Gly Asn Leu Leu Pro Asn Leu Thr
            570                 575                 580

GAC AAG GAC ATA AAG AGG TGC CGC TTC CAC CCT GAA AAG GCC CCA TTT        798
Asp Lys Asp Ile Lys Arg Cys Arg Phe His Pro Glu Lys Ala Pro Phe
585                 590                 595                 600

TGC CCC ATC TTG AGG GTA GGG GAT GTG GTT AAG TTT GCT GGA CAG GAT        846
Cys Pro Ile Leu Arg Val Gly Asp Val Val Lys Phe Ala Gly Gln Asp
                605                 610                 615

TTT GCC AAG CTG GCC CGC ACG GGT GGC GTT CTG GGT ATT AAG ATC GGC        894
Phe Ala Lys Leu Ala Arg Thr Gly Gly Val Leu Gly Ile Lys Ile Gly
            620                 625                 630

TGG GTG TGC GAT CTA GAC AAG GCC TGG GAC CAG TGC ATC CCT AAA TAT        942
Trp Val Cys Asp Leu Asp Lys Ala Trp Asp Gln Cys Ile Pro Lys Tyr
            635                 640                 645

TCC TTC ACT CGG CTG GAT GGA GTT TCT GAG AAA AGC AGT GTT TCC CCT        990
Ser Phe Thr Arg Leu Asp Gly Val Ser Glu Lys Ser Ser Val Ser Pro
650                 655                 660

GGC TAC AAC TTC AGG TTT GCC AAA TAC TAT AAG ATG GAG AAC GGC AGC       1038
Gly Tyr Asn Phe Arg Phe Ala Lys Tyr Tyr Lys Met Glu Asn Gly Ser
665                 670                 675                 680

GAG TAC CGC ACA CTC CTG AAG GCT TTT GGC ATC CGC TTT GAT GTG CTG       1086
Glu Tyr Arg Thr Leu Leu Lys Ala Phe Gly Ile Arg Phe Asp Val Leu
            685                 690                 695

GTA TAT GGG AAC GCT GGC AAG TTC AAC ATC ATC CCC ACC ATT ATC AGC       1134
Val Tyr Gly Asn Ala Gly Lys Phe Asn Ile Ile Pro Thr Ile Ile Ser
            700                 705                 710

TCG GTG GCG GCC TTC ACT TCT GTG GGA GTG GGC ACT GTT CTC TGT GAC       1182
Ser Val Ala Ala Phe Thr Ser Val Gly Val Gly Thr Val Leu Cys Asp
            715                 720                 725

ATC ATC CTG CTC AAT TTC CTC AAA GGG GCT GAT CAC TAC AAA GCC AGG       1230
Ile Ile Leu Leu Asn Phe Leu Lys Gly Ala Asp His Tyr Lys Ala Arg
730                 735                 740

AAG TTT GAG GAG GTG ACT GAG ACA ACA CTG AAG GGT ACT GCG TCA ACC       1278
Lys Phe Glu Glu Val Thr Glu Thr Thr Leu Lys Gly Thr Ala Ser Thr
745                 750                 755                 760

AAC CCA GTG TTC GCC AGT GAC CAG GCC ACT GTG GAG AAG CAG TCT ACA       1326
Asn Pro Val Phe Ala Ser Asp Gln Ala Thr Val Glu Lys Gln Ser Thr
            765                 770                 775

GAC TCA GGG GCC TAT TCT ATT GGT CAC TAGGGCCTCT TCCCAGGGTT            1373
Asp Ser Gly Ala Tyr Ser Ile Gly His
            780                 785

CCATGCTCAC CCTTAGGCTG CAGAACCTGC AAACAGGCCA CTCTATCTAA GCAGTCAGGG    1433

GTGGGAGGGG GAGAAGAAGG GCTGCTATTT CTGCTGTTCA CCCCAAAGAC TAGATCCAGA    1493

TATCTAGGCC CTCACTGTTC AACAGATAGG CAATGCTTCC CACTAAGACT TGAATCTTGC    1553

CTTTACCCCT TGCATGCCTC CCACCTGCTT CCCTGGATCC CAGGACAGCA GCATCCACCC    1613

CTTTCCAAAG GATTGAGAAA ATGGTAGCTA AGGTTACACC CATAGGACCT ACCACGTACC    1673

AAGCACTTCC ACACATATTA TCCCTTTTCA CCCTTAAAAT AATCCTATAA GGTAGAAAAA    1733
```

AAAAAAAAAA AAAAAAAAAA                                              1753

(2) INFORMATION FOR SEQ ID NO: 9:

(i) SEQUENCE CHARACTERISTICS:
        (A) LENGTH: 397 amino acids
        (B) TYPE: amino acid
        (D) TOPOLOGY: linear (ii) MOLECULE TYPE: protein (xi) SEQUENCE DESCRIPTION: SEQ ID NO: 9:

```
Met Asn Cys Ile Ser Asp Phe Phe Thr Tyr Glu Thr Thr Lys Ser Val
 1               5                  10                  15

Val Val Lys Ser Trp Thr Ile Gly Ile Ile Asn Arg Ala Val Gln Leu
            20                  25                  30

Leu Ile Ile Ser Tyr Phe Val Gly Trp Val Phe Leu His Glu Lys Ala
            35                  40                  45

Tyr Gln Val Arg Asp Thr Ala Ile Glu Ser Ser Val Val Thr Lys Val
            50                  55                  60

Lys Gly Phe Gly Arg Tyr Ala Asn Arg Val Met Asp Val Ser Asp Tyr
 65                  70                  75                  80

Val Thr Pro Pro Gln Gly Thr Ser Val Phe Val Ile Ile Thr Lys Met
                 85                  90                  95

Ile Val Thr Glu Asn Gln Met Gln Gly Phe Cys Pro Glu Asn Glu Glu
                100                 105                 110

Lys Tyr Arg Cys Val Ser Asp Ser Gln Cys Gly Pro Glu Arg Phe Pro
            115                 120                 125

Gly Gly Gly Ile Leu Thr Gly Arg Cys Val Asn Tyr Ser Ser Val Leu
130                 135                 140

Arg Thr Cys Glu Ile Gln Gly Trp Cys Pro Thr Glu Val Asp Thr Val
145                 150                 155                 160

Glu Met Pro Ile Met Met Glu Ala Glu Asn Phe Thr Ile Phe Ile Lys
                165                 170                 175

Asn Ser Ile Arg Phe Pro Leu Phe Asn Phe Glu Lys Gly Asn Leu Leu
            180                 185                 190

Pro Asn Leu Thr Asp Lys Asp Ile Lys Arg Cys Arg Phe His Pro Glu
            195                 200                 205

Lys Ala Pro Phe Cys Pro Ile Leu Arg Val Gly Asp Val Val Lys Phe
210                 215                 220

Ala Gly Gln Asp Phe Ala Lys Leu Ala Arg Thr Gly Gly Val Leu Gly
225                 230                 235                 240

Ile Lys Ile Gly Trp Val Cys Asp Leu Asp Lys Ala Trp Asp Gln Cys
                245                 250                 255

Ile Pro Lys Tyr Ser Phe Thr Arg Leu Asp Gly Val Ser Glu Lys Ser
            260                 265                 270

Ser Val Ser Pro Gly Tyr Asn Phe Arg Phe Ala Lys Tyr Tyr Lys Met
            275                 280                 285

Glu Asn Gly Ser Glu Tyr Arg Thr Leu Leu Lys Ala Phe Gly Ile Arg
            290                 295                 300

Phe Asp Val Leu Val Tyr Gly Asn Ala Gly Lys Phe Asn Ile Ile Pro
305                 310                 315                 320

Thr Ile Ile Ser Ser Val Ala Ala Phe Thr Ser Val Gly Val Gly Thr
                325                 330                 335

Val Leu Cys Asp Ile Ile Leu Leu Asn Phe Leu Lys Gly Ala Asp His
                340                 345                 350
```

```
Tyr Lys Ala Arg Lys Phe Glu Glu Val Thr Glu Thr Thr Leu Lys Gly
            355                 360                 365

Thr Ala Ser Thr Asn Pro Val Phe Ala Ser Asp Gln Ala Thr Val Glu
        370                 375                 380

Lys Gln Ser Thr Asp Ser Gly Ala Tyr Ser Ile Gly His
385                 390                 395
```

(2) INFORMATION FOR SEQ ID NO: 10:

(i) SEQUENCE CHARACTERISTICS:
        (A) LENGTH: 2643 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 10:

```
GCCTCCAGCT GACCTCTGGC TCCTGTCCTC TGGCTCCACC TGCACCGCCC TGCTCTTCCT      60

AAGGGGCCAG GAAGCCCCCA GAAGCTCTAC CATCGACGTG GGTGGTGGCA CCCGGCTCAC     120

CCTGAGAGCA GAGGGCGTGC AGGGGGCTCA GTTCTGAGCC CAGCCGGCCC ACC ATG        176
                                                           Met

GCA CGG CGG TTC CAG GAG GAG CTG GCC GCC TTC CTC TTC GAG TAT GAC       224
Ala Arg Arg Phe Gln Glu Glu Leu Ala Ala Phe Leu Phe Glu Tyr Asp
    400                 405                 410

ACC CCC CGC ATG GTG CTG GTG CGT AAT AAG AAG GTG GGC GTT ATC TTC       272
Thr Pro Arg Met Val Leu Val Arg Asn Lys Lys Val Gly Val Ile Phe
415                 420                 425                 430

CGA CTG ATC CAG CTG GTG GTC CTG GTC TAC GTC ATC GGG TGG GTG TTT       320
Arg Leu Ile Gln Leu Val Val Leu Val Tyr Val Ile Gly Trp Val Phe
                435                 440                 445

CTC TAT GAG AAG GGC TAC CAG ACC TCG AGC GGC CTC ATC AGC AGT GTC       368
Leu Tyr Glu Lys Gly Tyr Gln Thr Ser Ser Gly Leu Ile Ser Ser Val
                450                 455                 460

TCT GTG AAA CTC AAG GGC CTG GCC GTG ACC CAG CTC CCT GGC CTC GGC       416
Ser Val Lys Leu Lys Gly Leu Ala Val Thr Gln Leu Pro Gly Leu Gly
                465                 470                 475

CCC CAG GTC TGG GAT GTG GCT GAC TAC GTC TTC CCA GCC CAG GGG GAC       464
Pro Gln Val Trp Asp Val Ala Asp Tyr Val Phe Pro Ala Gln Gly Asp
            480                 485                 490

AAC TCC TTC GTG GTC ATG ACC AAT TTC ATC GTG ACC CCG AAG CAG ACT       512
Asn Ser Phe Val Val Met Thr Asn Phe Ile Val Thr Pro Lys Gln Thr
495                 500                 505                 510

CAA GGC TAC TGC GCA GAG CAC CCA GAA GGG GGC ATA TGC AAG GAA GAC       560
Gln Gly Tyr Cys Ala Glu His Pro Glu Gly Gly Ile Cys Lys Glu Asp
                515                 520                 525

AGT GGC TGT ACC CCT GGG AAG GCC AAG AGG AAG GCC CAA GGC ATC CGC       608
Ser Gly Cys Thr Pro Gly Lys Ala Lys Arg Lys Ala Gln Gly Ile Arg
                530                 535                 540

ACG GGC AAG TGT GTG GCC TTC AAC GAC ACT GTG AAG ACG TGT GAG ATC       656
Thr Gly Lys Cys Val Ala Phe Asn Asp Thr Val Lys Thr Cys Glu Ile
                545                 550                 555

TTT GGC TGG TGC CCC GTG GAG GTG GAT GAC GAC ATC CCG CGC CCT GCC       704
Phe Gly Trp Cys Pro Val Glu Val Asp Asp Asp Ile Pro Arg Pro Ala
            560                 565                 570

CTT CTC CGA GAG GCC GAG AAC TTC ACT CTT TTC ATC AAG AAC AGC ATC       752
Leu Leu Arg Glu Ala Glu Asn Phe Thr Leu Phe Ile Lys Asn Ser Ile
575                 580                 585                 590

AGC TTT CCA CGC TTC AAG GTC AAC AGG CGC AAC CTG GTG GAG GAG GTG       800
Ser Phe Pro Arg Phe Lys Val Asn Arg Arg Asn Leu Val Glu Glu Val
                595                 600                 605
```

```
AAT GCT GCC CAC ATG AAG ACC TGC CTC TTT CAC AAG ACC CTG CAC CCC      848
Asn Ala Ala His Met Lys Thr Cys Leu Phe His Lys Thr Leu His Pro
            610                 615                 620

CTG TGC CCA GTC TTC CAG CTT GGC TAC GTG GTG CAA GAG TCA GGC CAG      896
Leu Cys Pro Val Phe Gln Leu Gly Tyr Val Val Gln Glu Ser Gly Gln
        625                 630                 635

AAC TTC AGC ACC CTG GCT GAG AAG GGT GGA GTG GTT GGC ATC ACC ATC      944
Asn Phe Ser Thr Leu Ala Glu Lys Gly Gly Val Val Gly Ile Thr Ile
    640                 645                 650

GAC TGG CAC TGT GAC CTG GAC TGG CAC GTA CGG CAC TGC AGA CCC ATC      992
Asp Trp His Cys Asp Leu Asp Trp His Val Arg His Cys Arg Pro Ile
655                 660                 665                 670

TAT GAG TTC CAT GGG CTG TAC GAA GAG AAA AAT CTC TCC CCA GGC TTC     1040
Tyr Glu Phe His Gly Leu Tyr Glu Glu Lys Asn Leu Ser Pro Gly Phe
                675                 680                 685

AAC TTC AGG TTT GCC AGG CAC TTT GTG GAG AAC GGG ACC AAC TAC CGT     1088
Asn Phe Arg Phe Ala Arg His Phe Val Glu Asn Gly Thr Asn Tyr Arg
            690                 695                 700

CAC CTC TTC AAG GTG TTT GGG ATT CGC TTT GAC ATC CTG GTG GAC GGC     1136
His Leu Phe Lys Val Phe Gly Ile Arg Phe Asp Ile Leu Val Asp Gly
        705                 710                 715

AAG GCC GGG AAG TTT GAC ATC ATC CCT ACA ATG ACC ACC ATC GGC TCT     1184
Lys Ala Gly Lys Phe Asp Ile Ile Pro Thr Met Thr Thr Ile Gly Ser
    720                 725                 730

GGA ATT GGC ATC TTT GGG GTG GCC ACA GTT CTC TGT GAC CTG CTG CTG     1232
Gly Ile Gly Ile Phe Gly Val Ala Thr Val Leu Cys Asp Leu Leu Leu
735                 740                 745                 750

CTT CAC ATC CTG CCT AAG AGG CAC TAC TAC AAG CAG AAG AAG TTC AAA     1280
Leu His Ile Leu Pro Lys Arg His Tyr Tyr Lys Gln Lys Lys Phe Lys
                755                 760                 765

TAC GCT GAG GAC ATG GGG CCA GGG GCG GCT GAG CGT GAC CTC GCA GCT     1328
Tyr Ala Glu Asp Met Gly Pro Gly Ala Ala Glu Arg Asp Leu Ala Ala
            770                 775                 780

ACC AGC TCC ACC CTG GGC CTG CAG GAG AAC ATG AGG ACA TCC              1370
Thr Ser Ser Thr Leu Gly Leu Gln Glu Asn Met Arg Thr Ser
        785                 790                 795

TGATGCTCGG GCCCCAACTC CTGACTGGGT GCAGCGTGAG GCTTCAGCCT GGAGCCCTGG   1430

TGGGTCCCAG CCAGGGCAGA GGGGCCTCCC CAGGAAGTCT CCTACCCTCT CAGCCAGGCA   1490

GAGAGCAGTT TGCCAGAAGC TCAGGGTGCA TAGTAGGAGA GACCTGTGCA AATCTGAGCT   1550

CCGGCTCCGA CCCCACACAC CCTGAGGGAG GCCTACCCTA GCCTCAGCCG CTCCTGGTGG   1610

GGGAATGGCT GGGGGTTGGG CAGGACCCTC CCACACACCT GCACCCTAGC TTCGTGCTTC   1670

TCTCTCCGGA CTCTCATTAT CCAACCCGCT GCCTCCATTT CTCTAGATCT GTGCTCTCCG   1730

ATGTGGCAGT CAGTAACCAT AGGTGACTAA ATTAAACTAA AATAAAATAG AATGAAACAC   1790

AAAATTCAAT TCCTCGGCTG AACTAGCCAC ATTTCAACTG CTCAGTAGAT ACGTGTGGTT   1850

AGTGGCTGCC ATACTGGACA GCTCGGGCA TTTTCACTGT CAAAGAAAGT TCTATTAGAC    1910

AGCCCTGCTT GAGCCCTGTT TCTTCCTGGC TTCGGTTTCC CTGGGAACT TATCGACAAT    1970

GCAAGCTCCT GGGCCCACCC CCAGACCTCC TGAACCAAAA GCTCCAGGGC TGGCCGTATG   2030

ATCTGTGTGG ATGGCAAACT CCCCAGGCCA TTCTGGGACC TAAGTTTAAG AAGTGCCGTC   2090

CTCGAACTTT CTGACTCTAA GCTCCTGAGC GGGAGTCAGA CTTAGCCCTG AGCCTGCACT   2150

TCCTGTTCAG GTGCAGACAC TGAACAGGGT CTCAAACACC TTCAGCATGT GTGTTGTGTG   2210

CTCACGTGCC ACACAGTGTC TCATGCACAC AACCCAGTGT ACACACCACC TACGTGCACA   2270

CAGCATCCTT CCACACTGTG TATGTGAACA GCTTGGGCCC TGCAAACACA ACCATCTACA   2330
```

```
CACATCTACA CCCCCAAGCA CACACACATG GTCCGTGCCA TGTCACCTCC ATAGGGAAAG      2390

GCTTCTCTCC AAGTGTGCCA GGCCAGGACA GCCCTCCCAG CCATGAATCC TTACTCAGCT      2450

ACCTCGGGTT GGGGTGGGAG CCCCAGCCAA ATCCTGGGCT CCCTGCCTGT GGCTCAGCCC      2510

CAGCTCCCAA GGCCTGCCTG GCTCTGTCTG AACAGAAGGT CTGGGGGAAG CGAGGGGTGG      2570

AGTACAATAA AGGGAATGAG GACAAACAAA AAAAAAAAAA AAAAAAAAAA AAAAAAAAA       2630

AAAAAAAAAA AAA                                                        2643
```

(2) INFORMATION FOR SEQ ID NO: 11:

(i) SEQUENCE CHARACTERISTICS:
        (A) LENGTH: 399 amino acids
        (B) TYPE: amino acid
        (D) TOPOLOGY: linear (ii) MOLECULE TYPE: protein (xi) SEQUENCE DESCRIPTION: SEQ ID NO: 11:

```
Met Ala Arg Arg Phe Gln Glu Glu Leu Ala Ala Phe Leu Phe Glu Tyr
 1               5                  10                  15

Asp Thr Pro Arg Met Val Leu Val Arg Asn Lys Lys Val Gly Val Ile
                20                  25                  30

Phe Arg Leu Ile Gln Leu Val Val Leu Val Tyr Val Ile Gly Trp Val
            35                  40                  45

Phe Leu Tyr Glu Lys Gly Tyr Gln Thr Ser Ser Gly Leu Ile Ser Ser
        50                  55                  60

Val Ser Val Lys Leu Lys Gly Leu Ala Val Thr Gln Leu Pro Gly Leu
 65                  70                  75                  80

Gly Pro Gln Val Trp Asp Val Ala Asp Tyr Val Phe Pro Ala Gln Gly
                85                  90                  95

Asp Asn Ser Phe Val Val Met Thr Asn Phe Ile Val Thr Pro Lys Gln
                100                 105                 110

Thr Gln Gly Tyr Cys Ala Glu His Pro Glu Gly Gly Ile Cys Lys Glu
            115                 120                 125

Asp Ser Gly Cys Thr Pro Gly Lys Ala Lys Arg Lys Ala Gln Gly Ile
        130                 135                 140

Arg Thr Gly Lys Cys Val Ala Phe Asn Asp Thr Val Lys Thr Cys Glu
145                 150                 155                 160

Ile Phe Gly Trp Cys Pro Val Glu Val Asp Asp Ile Pro Arg Pro
                165                 170                 175

Ala Leu Leu Arg Glu Ala Glu Asn Phe Thr Leu Phe Ile Lys Asn Ser
                180                 185                 190

Ile Ser Phe Pro Arg Phe Lys Val Asn Arg Arg Asn Leu Val Glu Glu
            195                 200                 205

Val Asn Ala Ala His Met Lys Thr Cys Leu Phe His Lys Thr Leu His
        210                 215                 220

Pro Leu Cys Pro Val Phe Gln Leu Gly Tyr Val Val Gln Glu Ser Gly
225                 230                 235                 240

Gln Asn Phe Ser Thr Leu Ala Glu Lys Gly Gly Val Val Gly Ile Thr
                245                 250                 255

Ile Asp Trp His Cys Asp Leu Asp Trp His Val Arg His Cys Arg Pro
                260                 265                 270

Ile Tyr Glu Phe His Gly Leu Tyr Glu Glu Lys Asn Leu Ser Pro Gly
            275                 280                 285

Phe Asn Phe Arg Phe Ala Arg His Phe Val Glu Asn Gly Thr Asn Tyr
```

-continued

```
            290                     295                     300
Arg His Leu Phe Lys Val Phe Gly Ile Arg Phe Asp Ile Leu Val Asp
305                     310                     315                     320

Gly Lys Ala Gly Lys Phe Asp Ile Ile Pro Thr Met Thr Thr Ile Gly
                325                     330                     335

Ser Gly Ile Gly Ile Phe Gly Val Ala Thr Val Leu Cys Asp Leu Leu
                340                     345                     350

Leu Leu His Ile Leu Pro Lys Arg His Tyr Tyr Lys Gln Lys Lys Phe
        355                     360                     365

Lys Tyr Ala Glu Asp Met Gly Pro Gly Ala Ala Glu Arg Asp Leu Ala
        370                     375                     380

Ala Thr Ser Ser Thr Leu Gly Leu Gln Glu Asn Met Arg Thr Ser
385                     390                     395
```